United States Patent
Naik et al.

[11] Patent Number: 6,159,988
[45] Date of Patent: *Dec. 12, 2000

[54] ARYLCYCLOALKYL DERIVATIVES, THEIR PRODUCTION AND THEIR USE

[75] Inventors: Ramachandra Ganapati Naik, Ankleshwar; Vilas Narayan Mumbaikar, Thane; Ravishankar Vasumathy, Mumbai; Aftab Dawoodbhai Lakdawala, Mumbai; Mandakini Bipin Alreja, Mumbai; Bansi Lal, Mumbai, all of India; Jürgen Blumbach, Wiesbaden, Germany; Klaus Ulrich Weithmann, Hofheim am Taunus, Germany; Robert Ryder Bartlett, Darmstadt, Germany; Kalpana Sanjay Joshi, Thane, India; Swati Bal-Tembe, Mumbai, India; Sadagopan Raghavan, Hyderabad, India

[73] Assignee: Hoeschst Aktiengesellschaft, Frankfurt am Main, Germany

[*] Notice: This patent is subject to a terminal disclaimer.

[21] Appl. No.: 09/106,110

[22] Filed: Jun. 29, 1998

Related U.S. Application Data

[60] Continuation-in-part of application No. 08/692,129, Aug. 5, 1996, Pat. No. 5,776,977, which is a division of application No. 08/444,518, May 19, 1995, Pat. No. 5,589,514, which is a continuation of application No. 08/002,863, Jan. 14, 1993, abandoned.

[30] Foreign Application Priority Data

Jan. 16, 1992 [EP] European Pat. Off. ............ 92 100 664

[51] Int. Cl.$^7$ .......................... A01N 37/00; A01N 43/06; A01N 43/08; A01N 37/02; A01N 37/34; A01N 37/12; A01N 37/44; A01N 43/40; A00N 47/06

[52] U.S. Cl. .......................... 514/317; 514/438; 514/461; 514/512; 514/520; 514/546; 514/551; 514/568; 514/676; 514/683; 546/239; 549/78; 549/501; 560/149; 560/173; 560/252; 560/255; 562/463; 568/311; 568/312; 568/314; 568/315; 568/316; 568/317; 568/329

[58] Field of Search .................................. 514/317, 438, 514/461, 512, 520, 546, 551, 568, 676, 683; 546/239; 549/78, 501; 560/149, 173, 252, 255; 562/463; 568/311, 312, 314, 315, 316, 317, 329

[56] References Cited

U.S. PATENT DOCUMENTS 5,776,977  7/1998  Naik et al. .............................. 514/532

*Primary Examiner*—Johann Richter
*Assistant Examiner*—Brian J. Davis
*Attorney, Agent, or Firm*—Finnegan, Henderson, Farabow, Garrett & Dunner, L.L.P.

[57] ABSTRACT

Compounds of formula I,

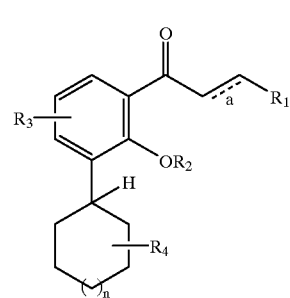

and the physiologically tolerable salts thereof, wherein the substituents $R_1$–$R_4$ have the meanings given in the specifications and show an activity against inflammatory conditions.

7 Claims, 5 Drawing Sheets

ARYLCYCLOALKYL DERIVATIVES, THEIR PRODUCTION AND THEIR USE

CROSS REFERENCE TO RELATED APPLICATIONS

This application is a continuation-in-part of application Ser. No. 08/692,129 filed Aug. 5, 1996 now U.S. Pat. No. 5,776,977, issued Jul. 7, 1998, which is a division of application Ser. No. 08/444,518 filed May 19, 1995, now U.S. Pat. No. 5,589,514 issued Dec. 31, 1996, which was a continuation of application Ser. No. 08/002,863 filed Jan. 14, 1993, abandoned, all of which are incorporated herein by reference.

BACKGROUND OF THE INVENTION

1. Field of the Invention

The present invention relates to novel arylcycloalkyl derivatives, their production, and their use.

2. Description of Related Art

The chalcones of the following general formula Ia are known by the following prior art:

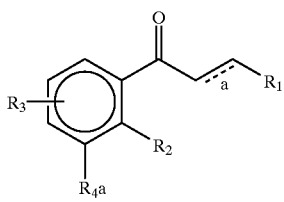

(Ia)

1. J.P. 281022—Compounds of formula Ia, wherein
   $R_1$=substituted phenyl,
   $R_2$=OH,
   a=single or double bond,
   $R_3$=OH,
   $R_{4a}$=H, isoprenyl or isopentyl,
   and are effective in treatment of diseases caused by hypersecretion of androgens, e.g., prostatomegaly, alopecia in males, acne vulgaris or seborrhoea.

2. J.P. 026775—Compounds of formula Ia wherein
   $R_1$=substituted phenyl,
   $R_2$=H, OH, acetoxy, carboxymethoxy or methoxycarbonylmethoxy,
   $R_3$=OH, methoxy, benzyloxy, H,
   $R_{4a}$=H, isoprenyl or isopentyl,
   and possess anti-hyaluronidase activity.

3. J.P. 142166—Compounds of formula Ia wherein
   $R_1$=substituted phenyl,
   $R_2$=OH, acetoxy, carboxymethoxy, methoxycarboxylmethoxy,
   $R_3$=OH, methoxy, H,
   a=single or a double bond,
   $R_{4a}$=isoprenyl, isopentyl, n-propyl or H,
   and are useful as aldose reductase inhibitors—used to treat diabetic complications such as cataracts, retinitis, nerve disorder or kidney disease.

4. J.P. 248389—Compounds of formula Ia wherein
   $R_1$=substituted phenyl,
   $R_2$=OH,
   $R_3$=OH,
   a=a double bond,
   $R_{4a}$=H,
   and are useful as aldose reductase inhibitors—for treatment of diabetes mellitus complications.

5. J.P. 144717—Compounds of formula Ia wherein
   $R_1$=substituted phenyl,
   $R_2$=H or OH,
   $R_3$=H or OH,
   a=a double bond,
   $R_{4a}$=H or OH,
   and are useful as c-kinase inhibitors and antitumor agents.

6. EP 150166—Compounds of formula Ia wherein
   $R_1$=substituted phenyl,
   $R_2$=H, halogen, lower alkyl, lower alkoxy, CN, carboxy, nitro,
   $R_3$=H, halogen, lower alkyl, lower alkoxy, CN, carboxy, nitro, hydroxy, substituted acetic acid derivative,
   a=a double bond,
   $R_{4a}$=as in $R_3$,
   and having inhibitory effect on hydroxy-prostaglandin dehydrogenase. They may have potential local activity against gastrointestinal disorders such as gastric ulcer, and ulcerative colitis. Other potential fields of application include the treatment of rheumatoid arthritis, circulatory disorders, cancer, lack of fertility and cell regulation.

7. J.P. 167288—Compounds of formula Ia wherein
   $R_1$=substituted phenyl,
   $R_2$=H,
   $R_3$=OH,
   a=a single bond,
   $R_{4a}$=OH,
   and are selective inhibitors of 5-lipoxygenase and have excellent anti-allergic activity, thus are useful as a safe anti-allergic drug such as antiasthmatic, antiphlogistic and immune activating drug.

BRIEF SUMMARY OF THE INVENTION

The present invention relates to compounds of formula I,

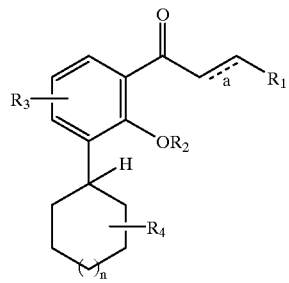

(I)

wherein $R_1$=$C_1$–$C_6$-alkyl, substituted $C_1$–$C_6$-alkyl, C(O)O—$C_1$–$C_4$-alkyl, C(O)OH, or a residue selected from

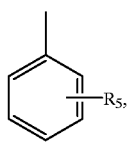 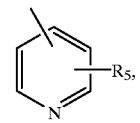 

-continued

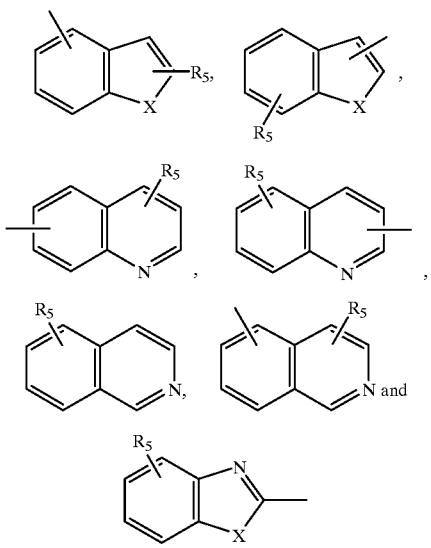

wherein R$_5$ is one, two, three, or four of the residues which are independent of each other and are selected from the group consisting of H, C$_1$–C$_6$-alkyl, substituted C$_1$–C$_6$-alkyl, hydroxy, C$_1$–C$_6$-alkoxy, carboxy, cyano, NHC(O)C$_1$–C$_3$-alkyl, —OC$_1$–C$_3$-alkyl-phenyl, —OCH$_2$—O—, C$_1$–C$_4$-alkyl-O—C$_1$–C$_4$-alkyl, —O—(O)—C$_1$–C$_4$-alkyl, —C(O)—O—C$_1$–C$_4$-alkyl, halogen, amino, nitro, —NH—C$_1$–C$_4$-alkyl, —N—(C$_1$–C$_4$-alkyl)$_2$, and —C$_1$–C$_4$-alkyl-R$_6$ wherein R$_6$ is a residue selected from

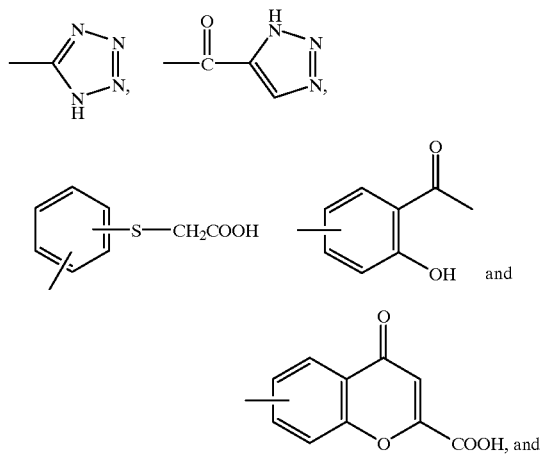

X is O, S, N—H, N—C$_1$–C$_6$-alkyl;

R$_2$ is H, C$_1$–C$_6$-alkyl, —C(O)—C$_1$–C$_6$-alkyl;

R$_3$ is one, two, or three of the residues which are independent of each other and are selected from the group consisting of H, C$_1$–C$_6$-alkyl, —C(O)—C$_1$–C$_6$-alkyl, —C(O)—O—C$_1$–C$_6$-alkyl, OH, O—C$_1$–C$_6$-alkyl, —O—C(O)—C$_1$–C$_6$-alkyl, halogen;

R$_4$ is H, —OH, —O—C$_1$–C$_6$-alkyl, —O—C(O)—C$_1$–C$_6$-alkyl, —C(O)—OH, —C(O)—O—C$_1$–C$_6$-alkyl, O—C(O)—(C$_1$–C$_4$-alkyl-NH$_2$, O—C(O)—(C$_1$–C$_4$-alkyl)-NH—(C$_1$–C$_4$-alkyl), O—C(O)—(C$_1$–C$_4$-alkyl)-N—(C$_1$–C$_4$-alkyl)$_2$;

n 0, 1 or 2; and a represents an optional additional single bond, and to the physiologically tolerable salts thereof.

Preferred compounds are compounds of formula II

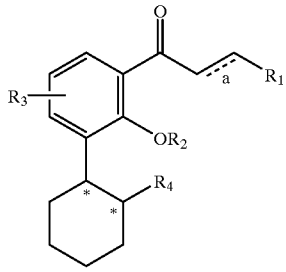

(II)

wherein R$_1$, R$_2$, R$_3$, R$_4$ and a are as previously defined, and the physiologically tolerable salts thereof.

Among this group of compounds, those are preferred in which R$_1$ is

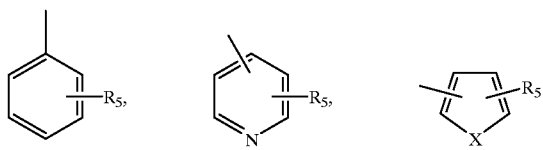

R$_5$ denoting H, C$_1$–C$_6$-alkyl, substituted C$_1$–C$_6$-alkyl, hydroxy, C$_1$–C$_3$-alkoxy, halogen, C$_1$–C$_4$-alkyl-R$_6$ wherein R$_6$ stands for

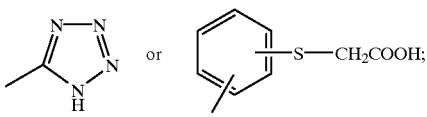

R$_4$ denotes H, OH or —O—C(O)—(C$_1$–C$_4$-alkyl)-NH$_2$;
X stands for O, NH, S, N—C$_1$–C$_6$-alkyl; and
a stands for an optional additional bond,
and the physiologically tolerable salts thereof.

Particularly preferred are compounds of formula III

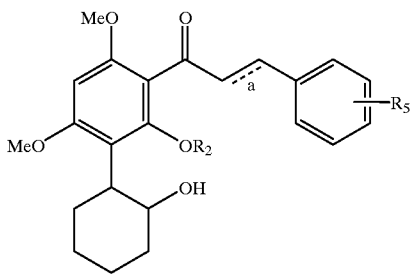

(III)

wherein
R$_2$ is H or C$_1$–C$_3$-alkyl,
R$_5$ denotes one or two halogens or one or two C$_1$–C$_6$-alkyl or C$_1$–C$_3$-alkoxy groups, and a denotes an optional additional single bond, and the physiologically tolerable salts thereof.

The above term substituted alkyl means alkyl, preferably $C_1$–$C_3$-alkyl, substituted by preferably one halogen, hydroxy, $C_1$–$C_3$-alkoxy, amino, $C_1$–$C_4$-alkylamino, di-($C_1$–$C_4$-alkyl)-amino, carbonyl or carboxy-$C_1$–$C_4$-alkyl.

The compounds of the invention contain two asymmetric centers, designated with asterisks in formula II, at the points of attachment of $R_4$, (e.g., formula II, when $R_4$=H) and of the aryl group on the carbocyclic ring; therefore, four isomers are possible, designated individually as the cis-(+), cis-(–), trans (+), and trans-(–) forms. The present invention includes each of the four isomers individually or as mixtures of two or more of the four isomers.

Examples of particularly preferred compounds are:
1. trans-(+/–)-2-[4,6-Dimethoxy-2-hydroxy-3-(3-(4-chlorophenyl))prop-2-enoyl]-phenylcyclohexanol.
2. trans-(+/–)-2-[4,6-Dimethoxy-2-hydroxy-3-(3-(2-chlorophenyl))prop-2-enoyl]-phenylcyclohexanol.
3. trans-(+/–)-2-[4,6-Dimethoxy-2-hydroxy-3-(3-(3-chlorophenyl))prop-2-enoyl]-phenylcyclohexanol.
4. trans-(+/–)-2-[4,6-Dimethoxy-2-hydroxy-3-(3-(2-bromophenyl))prop-2-enoyl]-phenylcyclohexanol.
5. trans-(+/–)-2-[4,6-Dimethoxy-2-hydroxy-3-(3-(3-bromophenyl))prop-2-enoyl]-phenylcyclohexanol.
6. trans-(+/–)-2-[4,6-Dimethoxy-2-hydroxy-3-(3-(4-bromophenyl))prop-2-enoyl]-phenylcyclohexanol.
7. trans-(+/–)-2-[4,6-Dimethoxy-2-hydroxy-3-(3-(4-fluorophenyl))prop-2-enoyl]-phenylcyclohexanol.
8. trans-(+/–)-2-[4,6-Dimethoxy-2-hydroxy-3-(3-(2-methylphenyl))prop-2-enoyl]-phenylcyclohexanol.
9. trans-(+/–)-2-[4,6-Dimethoxy-2-hydroxy-3-(3-(4-methylphenyl))prop-2-enoyl]-phenylcyclohexanol.
10. trans-(+/–)-2-[4,6-Dimethoxy-2-hydroxy-3-(3-(2,3-dichlorophenyl))prop-2-enoyl]-phenylcyclohexanol.
11. trans-(+/–)-2-[4,6-Dimethoxy-2-hydroxy-3-(3-(2,6-dichlorophenyl))prop-2-enoyl]-phenylcyclohexanol.
12. trans-(+/–)-2-[4,6-Dimethoxy-2-hydroxy-3-(3-(2,6-dichlorophenyl))prop-2-enoyl]-phenylcyclohexanol.
13. trans-(+)-2-[4,6-Dimethoxy-2-hydroxy-3-(3-(4-chlorophenyl))prop-2-enoyl]phenylcyclohexanol.
14. trans-(–)-2-[4,6-Dimethoxy-2-hydroxy-3-(3-(4-chlorophenyl))prop-2-enoyl]phenylcyclohexanol.
15. trans-(+/–)-2-[4,6-Dimethoxy-2-hydroxy-3-(3-(3-methoxyphenyl))prop-2-enoyl]phenylcyclohexanol.
16. trans-(–)-2-[4,6-Dimethoxy-2-hydroxy-3-(3-(3-methoxyphenyl))prop-2-enoyl]phenylcyclohexanol.
17. trans-(+/–)-2-[4,6-Dimethoxy-2-hydroxy-3-(3-(4-chloro-3-nitrophenyl))prop-2-enoyl]phenylcyclohexanol.
18. trans-(–)-2-[4,6-Dimethoxy-2-hydroxy-3-(3-(4-chloro-3-nitrophenyl))prop-2-enoyl]phenylcyclohexanol.
19. trans-(+/–)-1-[4,6-Dimethoxy-2-hydroxy-3-(2-(β-amino)acetoxy)cyclohexyl]phenyl-1-(3-(3,4-dimethoxy)phenyl)propanone hydrochloride.
20. trans(–)-2-[4,6-Dimethoxy-2-hydroxy-3-(3-(3-bromophenyl)prop-2-enoyl)-phenyl]cyclohexyl-2-(S)-carb-tertbutoxyamino propanoate hydrochloride.

Further examples of particularly preferred compounds are:
21. trans-(+/–)-2-[4,6-Dimethoxy-2-hydroxy-3-(3-(3-bromophenyl)prop-2-(E)-enoyl)phenyl]cyclohexyl-2-amino acetate hydrochloride monohydrate.
22. trans-(–)-2-[4,6-Dimethoxy-2-hydroxy-3-(3-(3-bromophenyl)prop-2-(E)-enoyl)phenyl]cyclohexyl-2-amino acetate hydrochloride monohydrate.
23. trans-(+)-2-[4,6-Dimethoxy-2-hydroxy-3-(3-(3-bromophenyl)prop-2-(E)-enoyl)phenyl]cyclohexyl-2-amino acetate hydrochloride monohydrate.
24. trans-(+/–)-2-[4,6-Dimethoxy-2-hydroxy-3-(3-(3-bromophenyl)prop-2-(E)-enoyl)phenyl]cyclohexyl-2-(S)-amino propanoate.
25. trans-(–)-2-[4,6-Dimethoxy-2-hydroxy-3-(3-(3-bromophenyl)prop-2-(E)-enoyl)phenyl]cyclohexyl-2-(S)-amino propanoate hydrochloride.
26. trans-(–)-2-[4,6-Dimethoxy-2-hydroxy-3-(3-(3-bromophenyl)prop-2-(E)-enoyl)phenyl]cyclohexyl-2-(S)-amino propanoate hydrochloride.
27. cis-(+/–)-2-[4,6-Dimethoxy-2-hydroxy-3-(3-(3-bromophenyl))prop-2-(E)-enoyl]phenylcyclohexanol.
28. trans-(–)-2-[4,6-Dimethoxy-2-hydroxy-3-(3-(3-bromophenyl))prop-2-(E)-enoyl]phenylcyclohexanol.
29. trans-(+)-2-[4,6-Dimethoxy-2-hydroxy-3-(3-(3-bromophenyl))prop-2-(E)-enoyl]phenylcyclohexanol.
30. trans-(+/–)-2-[6-Methoxy-2-hydroxy-3-(3-(3-bromophenyl))prop-2-(E)-enoyl]phenylcyclohexanol.
31. trans-(+/–)-2-[2,6-Dimethoxy-4-hydroxy-3-(3-(3-bromophenyl))prop-2-(E)-enoyl]phenylcyclohexanol.
32. trans-(+/–)-2-[2-Hydroxy-4-methoxy-3-(3-(3-bromophenyl))prop-2-(E)-enoyl)phenylcyclohexanol hemihydrate.
33. trans-(+/–)-1-[4,6-Dimethoxy-2-hydroxy-3-(2-(β-amino)acetoxy)cyclohexyl]phenyl-(3-(3,4-dimethoxy)phenyl)propanone hydrochloride monohydrate.
34. trans-(+/–)-2-[4,6-Dimethoxy-2-hydroxy-3-(3-(2,5-dimethylphenyl))prop-2-(E)-enoyl]phenylcyclohexanol monohydrate.

A further subject of the instant application is a process for the production of compounds of formula I as described above wherein a compound of formula V

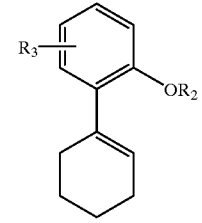

(V)

A) is converted into a compound of formula VI,

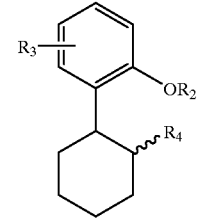

(VI)

$R_4$ denoting OH by treatment with a borane-solvent-complex followed by oxidation or B) to get a compound of formula VI, a compound of formula V is treated with a peracid and the epoxide thus produced is treated with a hydride reagent or C) the compound of formula VI is produced by condensation of a suitable arene with cyclohexene oxide in the presence of an acid catalyst and D) a compound of formula VI is treated with acetic anhydride and a mineral acid to give a compound of formula VII,

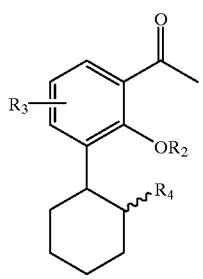

(VII)

wherein $R_2$ is methyl and $R_4$ is O—C(O)—Me and

E) a compound of formula VII as described under D) is demethylated by treatment with a Lewis acid or a demethylating agent to give a compound of formula VII wherein $R_2$ denotes H and $R_4$ denotes OC(O)Me and F) a compound of formula VII wherein $R_2$ denotes H and $R_4$ denotes OH is produced by treatment of a compound produced under E) with dilute alkali, and G) the compound of formula VII is converted into a compound of formula I (a=additional bond) by treatment with an appropriate aldehyde in the presence of a base and the compound of formula I (a=no additional bond) is produced by hydrogenation of the compound of formula I (a=additional bond), $R_1$, $R_2$ and $R_3$, where not explained explicitly, having the meaning as indicated above.

H) a compound of the formula II wherein $R_4$ is an amino acid ester can be prepared by treating a compound of the formula II (wherein $R_4$ is —OH) with an appropriate N-protected amino acid in the presence of dicyclohexyl carbodiimide and a weak base, for example, 2,4-dimethyl amino pyridine. The ester obtained can be subjected to deprotection of the amino function using a weak acid. The weak acid can be formic acid in the presence of anisaldehyde. The formate salt can be exchanged with the hydrochloride salt.

The compounds of formula V are prepared by methods known to a person skilled in the art. Typically, they are prepared by addition of aryllithiums of formula IV to cyclohexanone followed by acid catalyzed dehydration, $R_2$ and $R_3$ having the meaning as indicated above.

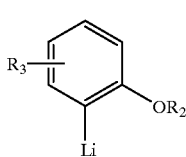

(IV)

A suitable borane-solvent complex for step A of the above sequence is, for instance, borane-tetrahydrofuran or borane dimethylsulfide. The oxidation can be carried out using alkaline hydrogen peroxide. A suitable peracid for step B is, for instance, chloroperbenzoic acid. An example of a suitable hydride reagent is lithium aluminum hydride.

Step C can be carried out using as arene, 1.3.5-trimethoxy-benzene, for example, the acid catalyst being aluminum chloride.

The mineral acid needed for step D can be, for instance, phosphoric acid.

Step E can be carried out using, for example, as Lewis acid boron tribromide and as demethylating agent, metal thiolates. The preferred dilute alkali for step F is 2N sodium hydroxide solution.

The base in the presence of which step G is carried out can be sodium hydroxide, for example.

The products according to the above reaction steps can be used for further reactions to compounds according to the instant invention. Most of said reactions can be carried out according to procedures described in European patent application 0 241 003. Additional information about starting products, intermediates and derivatization reactions can be obtained from the patent literature mentioned in the introduction.

The physical constants of some of the preferred compounds of the present invention are listed in Tables 1, 1A and 2.

TABLE 1

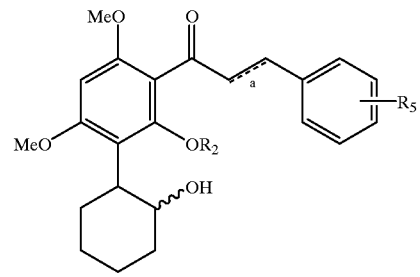

| Compound No. | $R_5$ | $R_2$ | a | m.p. ° C. | Sign of Rotation |
|---|---|---|---|---|---|
| 1. | H | H | Δ 2',3' | 183–185 | ± |
| 2. | 2-Cl | H | " | 204–206 | " |
| 3. | 3-Cl | H | " | 170 | " |
| 4. | 4-Cl | H | " | 221 | " |
| 5. | 2-Br | H | " | 203 | " |
| 6. | 3-Br | H | " | 171 | " |
| 7. | 4-Br | H | " | 222 | " |
| 8. | 4-F | H | " | 215–216 | " |
| 9. | 2,3-Cl$_2$ | H | " | 216 | " |
| 10. | 2,4-Cl$_2$ | H | " | 226–228 | " |
| 11. | 2,6-Cl$_2$ | H | " | 197 | " |
| 12. | 2-Me | H | " | 199 | " |
| 13. | 4-Me | H | " | 213 | " |
| 14. | 4-OMe | H | " | 210 | " |
| 15. | 4-Cl | Me | " | 175 | " |
| 16. | 4-Cl | H | H,H | 190 | " |
| 17. | 4-F | H | H,H | 169 | " |
| 18. | 3,4-Cl$_2$ | H | Δ2',3' | 202 | " |
| 19. | 3,5-Cl$_2$ | H | " | 227 | " |
| 20. | 2-OMe | H | " | 215 | " |
| 21. | 3-OMe | | " | 178 | " |
| 22. | 3,4-(OMe)$_2$ | H | " | 194 | " |
| 23. | 2,5-(OMe)$_2$ | H | " | 185 | " |
| 24. | 2,4-(OMe)$_2$ | H | " | 224–225 | " |
| 25. | 2,4,6-(OMe)$_3$ | H | " | 162 | " |
| 26. | 4-COOH | H | " | 240 | " |
| 27. | 4-N(CH$_3$)$_2$ | H | " | 187 | " |
| 28. | 4 Cl,3-NO$_2$ | H | " | 215 | " |
| 29. | 3-OH | H | " | 210 | " |
| 30. | 4-OH | H | " | 210 | " |

TABLE 1-continued

[Chemical structure: trimethoxyphenyl chalcone with cyclohexanol substituent and R5-substituted phenyl ring]

| Compound No. | $R_5$ | $R_2$ | a | m.p. °C. | Sign of Rotation |
|---|---|---|---|---|---|
| 31. | 2-OH | H | " | 209 | " |
| 32. | 4-$CF_3$ | H | " | 177 | " |
| 33. | 4-$NHCOCH_3$ | H | " | 274 | " |
| 34. | 3,4-$(OMe)_2$ | H | H,H | 151 | " |
| 35. | 2,4,6-$(OMe)_3$ | H | H,H | 132 | " |
| 36. | 2-OH | H | H,H | 190 | " |
| 37. | 3-OH | H | H,H | 63 | " |
| 38. | 4-OH | H | H,H | 216 | " |
| 39. | 3,4-$(OH)_2$ | H | H,H | 201 | " |
| 40. | 2-$CH_3$ | H | H,H | 157 | " |
| 41. | 3,4-$(OCH_2Ph)_2$ | H | Δ'2,'3 | 173 | " |
| 42. | 3,4-O—$CH_2$—O— | H | Δ'2,'3 | 185 | " |
| 43. | 4-Cl | H | " | 231 | (+) |
| 44. | 4-Cl | H | " | 231 | (−) |
| 45. | 4-Cl,3-$NO_2$ | H | " | 235 | (+) |
| 46. | 4-Cl,3-$NO_2$ | H | " | 235 | (−) |
| 47. | 3-OMe | H | " | 191 | (+) |
| 48. | 3-OMe | H | " | 191 | (−) |
| 49. | 3,4-$(OMe)_2$ | H | " | 195 | (+) |
| 50. | 3,4-$(OMe)_2$ | H | " | 195 | (−) |
| 51. | 2,3-$Cl_2$ | H | " | 217 | (+) |
| 52. | 2,3-$Cl_2$ | H | " | 217 | (−) |

TABLE 1A

Compounds of formula II in which $R_3$ = 4,6-$(OCH_3)_2$

| Compound No. | $R_1$ | a | $R_2$ | $R_4$ | m.p. °C. | Sign of Rotation |
|---|---|---|---|---|---|---|
| 1. | 2-Thienyl | Δ2',3' | H | OH | 179–180 | |
| 2. | 2-Furyl | " | H | OH | | (±) |
| 3. | 4-Nitrophenyl | " | H | —$OCOCH_3$ | 175 | " |
| 4. | 4-Cyanophenyl | " | H | —$OCOCH_3$ | 172 | " |
| 5. | 4-Chlorophenyl | " | H | —$OCOCH_2NH_2$—HCl | 152 | " |
| 6. | 3,4-Dimethoxy-phenyl | " | H | —$OCOCH_2NH_2$—HCl | 136–138 | " |

The physical constants of further preferred compounds of the present invention are listed in Table 2.

TABLE 2

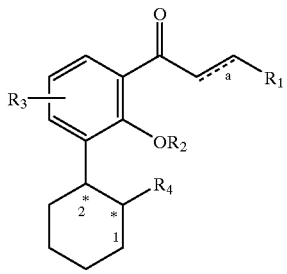

(II)

| No | $R_1$ | a | $R_2$ | $R_3$ | $R_4$ | *1 | *2 m.p. °C. | Rot | Activity (Concn.) IL-1 Rel. Inhib. |
|---|---|---|---|---|---|---|---|---|---|
| 1 | 3-Bromophenyl | $\Delta 2',3'$ | H | 4,6-$(OCH_3)_2$ | —$OCOCH_3$ | trans | 173–74 | (+/−) | 41% (10 μM) |
| 2 | 3-Bromophenyl | " | H | " | —$OCOCH_2N(CH_3)_2$.HCl | " | 217–18 | (+/−) | 50% (17 μM) |
| 3 | 3-Bromophenyl | " | H | " | —$OCOCH_2NH_2$.HCl | " | 140–42 | (+/−) | 63% (17 μM) |
| 4 | 3-Bromophenyl | " | H | " | —$OCOCH_2N\text{(piperidine)}$.HCl | " | 224–47 | (+/−) | 43% (16 μM) |
| 5 | 3-Bromophenyl | " | H | " | —$OCOCH_2NH_2$.HCl | R,S | 139–41 | (−) | 95% (1 μM) |
| 6 | 3-Bromophenyl | " | H | " | —$OCOCH_2NH_2$.HCl | S,R | 138–39 | (+) | 88% (1 μM) |
| 7 | 3-Bromophenyl | " | H | " | —OCO—(S)—$CH(NH_2)CH_3$.HCl | trans | 122–24 | (+/−) | 35% (1 μM) |
| 8 | 3-Bromophenyl | " | H | " | —OCO—(S)—$CH(NH_2)CH(CH_3)_2$.HCl | " | | (+/−) | ND |
| 9 | 3-Bromophenyl | " | H | " | —OCO—(S)—$CH(NH_2)CH_3$.HCl | R,S | 138–40 | (−) | 55% (5 μM) |
| 10 | 3-Bromophenyl | " | H | " | —OCO—$CH(NH_2)CH_3$.HCl | S,R | 130–32 | (−) | 72% (5 μM) |
| 11 | 3-Bromophenyl | $\Delta 2',3'$ | H | 4,6-$(OCH_3)_2$ | —OH | cis | 175–76 | (+/−) | 90% (10.8 μM) |
| 12 | 3-Bromophenyl | H,H | H | " | —OH | trans | 124–25 | (+/−) | 26% (10.5 μM) |
| 13 | 3-Bromophenyl | $\Delta 2',3'$ | H | 4-OH,6-$OCH_3$ | —OH | " | 215–17 | (+/−) | 22% (11.6 μM) |
| 14 | 3-Bromophenyl | " | H | 4,6-$(OCH_3)_2$ | —OH | R,S | 156–57 | (−) | 50% (0.3 μM) |
| 15 | 3-Bromophenyl | " | H | " | —OH | S,R, | 154 | (+) | 50% (0.3 μM) |
| 16 | 3-Bromophenyl | " | H | 6-$OCH_3$ | —OH | trans | 148–50 | (+/−) | 81% (11.6 μM) |
| 17 | 3-Bromophenyl | " | $CH_3$ | 4-OH,6-$OCH_3$ | —OH | " | 141–42 | (+/−) | 71% (10.8 μM) |
| 18 | 3-Bromophenyl | " | H | 4-$OCH_3$ | —OH | " | 164 | (+/−) | 71% (5 μM) |
| 19 | 3,4-Dimethoxyphenyl | H,H | H | 4,6-$(OCH_3)_2$ | —$OCOCH_2NH_2$.HCl | " | 136–38 | (+/−) | 51% (10 μM) |
| 20 | 3-Methylphenyl | $\Delta 2',3'$ | H | " | —OH | " | 148 | (+/−) | 49% (10 μM) |
| 21 | 2,5-Dimethylphenyl | " | H | " | —OH | " | 197 | (+/−) | 96% (10 μM) |
| 22 | 4-Chlorophenyl | " | H | " | H | — | 208 | (+/−) | 30% (12 μM) |
| 23 | 2,4-Dimethyl phenyl | " | H | " | —OH | trans | 211 | (+/−) | ND |
| 24 | 4-Methylphenyl | H,H | H | " | —OH | " | 165 | (+/−) | ND |
| 25 | 3-Methoxy phenyl | H,H | H | " | —OH | " | 112 | (+/−) | ND |
| 26 | 3-Bromo-4,5-Dimethoxyphenyl | $\Delta 2',3'$ | H | " | —OH | " | 135 | (+/−) | 50% (9.5 μM) |
| 27 | 3-Bromophenyl | " | H | " | —OH | " | 74–76 | (+/−) | 52% (1 μM) |
| 28 | 3-Aminophenyl | " | H | " | —OH | " | 152–58 | (+/−) | 33% (1 μM) |

The novel compounds of the present invention display interesting pharmacological activity when tested in pharmacological models; Compound Nos. 4 and 6 of Table 1 will be used in the examples as representative compounds.

As shown in the examples, the instant compounds have antiinflammatory properties. The compounds are particularly useful to inhibit or antagonize the responses mediated by endogenous molecules such as lipoxygenases and/or leukotrienes, interleukins and protein kinase C. The compounds of the invention, alone or in the form of a suitable formulation, are thus useful as medicaments in the treatment of inflammatory conditions, in particular chronic inflammatory conditions such as rheumatoid arthritis, osteoarthritis, asthma and malignancies.

Accordingly, other subjects of the instant invention are the use and methods of use to treat and prevent the above-mentioned inflammatory conditions by administration of an effective amount of one or more compounds of the instant invention. Furthermore, pharmaceuticals containing one or more compounds as explained above are a subject of this invention. Said pharmaceuticals can be produced and administered according to methods known in the art.

Figure 1:
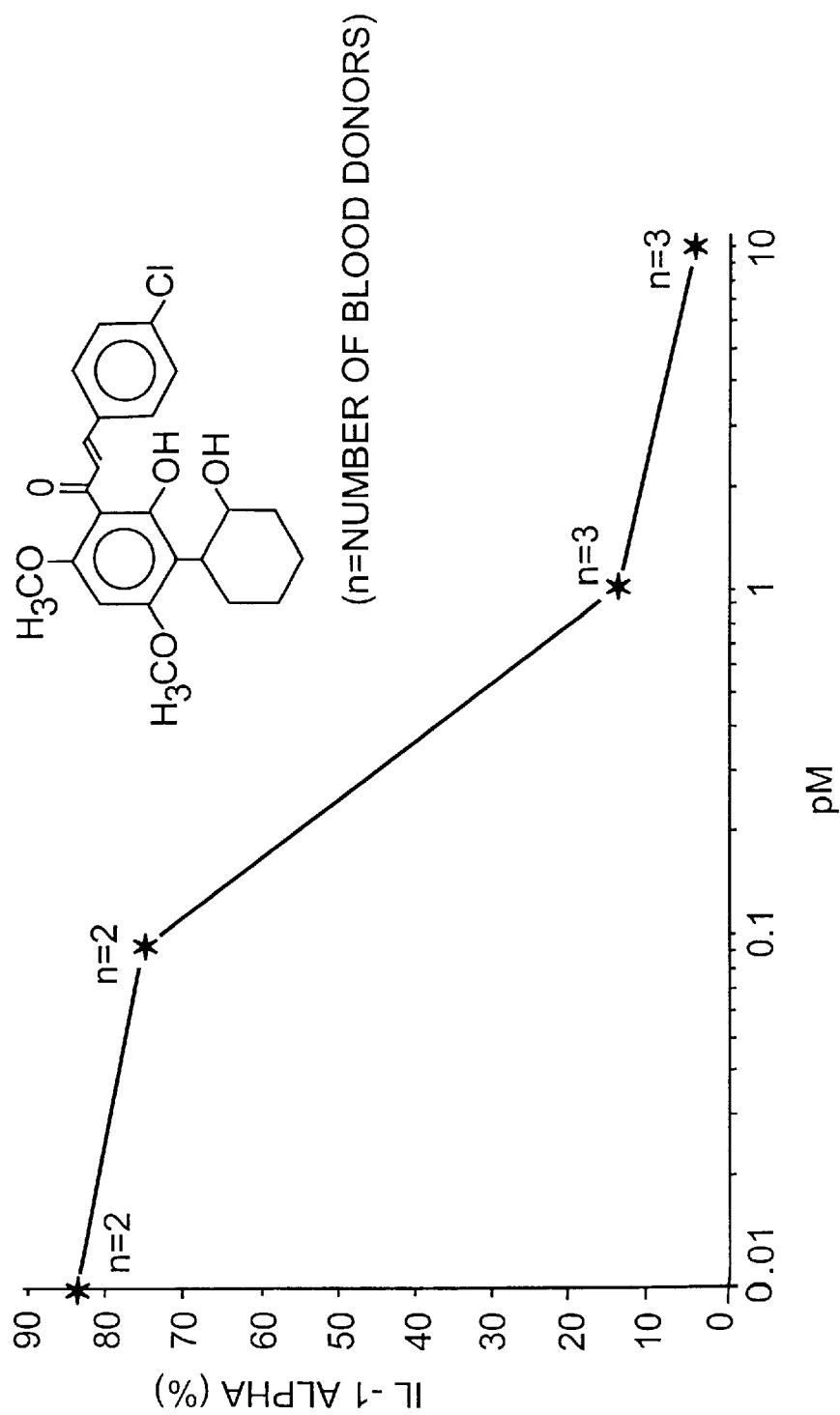
FIG. 1 is a graph illustrating the effect of Compound 4 of Table 1 as inhibitor of LPS stimulated IL-1 alpha.

The following examples as well as the appended claims further illustrate the instant invention.

DETAILED DESCRIPTION OF THE INVENTION

EXAMPLE 1

Inhibition of Leukotriene Induced Contraction of Isolated Guinea Pig Ileum

Guinea pigs of either sex weighing 300–350 g were sensitized with a suspension of aluminum hydroxide gel and egg albumin. After 21 days, each animal was exposed to 0.5% egg albumin aerosol in an air tight perspex chamber and only those animals which developed allergic bronchoconstriction were selected for further experiment.

The animals were tested for one week after antigenic exposure and then sacrificed by head blow and cutting carotid arteries. The lung was quickly removed and placed in aerated Tyrode solution kept at 37° C. The lung was cut into uniform strips and each strip was placed in an organ bath containing isolated guinea pig ileum connected to potentiometric recorder through isotonic transducer in the presence of Tyrode solution kept at 37° C. After a stabilizing period of 30 minutes, the reactivity of ileum to histamine was confirmed by challenging it with 100 ng–200 ng/ml of histamine. The perfusion fluid was then replaced by Tyrode solution containing Atropine ($10^{-7}$ M), Mepyramine maleate ($10^{-7}$ M) and methylsergide ($10^{-7}$ M). Three minutes later, lung strip was challenged by egg albumin (25 $\mu$g/ml) and release of leukotrienes was monitored in terms of slow contraction of ileum. The ileum was allowed to contract for 10–15 minutes when a plateau was achieved. The test compound (compound 4 of Table 1) was then added to observe the relaxation.

The specificity of leukotriene antagonism was determined by inducing contraction of guinea pig ileum with agonists like histamine, acetylcholine and KC1. Compounds having specific effect against lipoxygenase products induced contraction normally would not show any inhibition of histamine, acetylcholine and KC1 induced contraction. The data are shown in Table 3.

TABLE 3

Effect of Compound No. 4 on isolated guinea pig ileum precontracted with leukotrienes.

| Conc. (M) | % Relaxation | App. IC$_{50}$ (M) |
| --- | --- | --- |
| 1.2 × 10$^{-6}$ | 36.8 | |
| 1.68 × 10$^{-6}$ | 50.5 | 1.68 × 10$^{-6}$ |
| 2.4 × 10$^{-6}$ | 62.4 | |
| 7.2 × 10$^{-6}$ | 68.0 | |

No effect on histamine and KC1 induced contraction up to 7.11×10$^{-5}$ M.

Compound 4 as representative of the novel compounds of the present invention inhibits the contractions induced by leukotrienes.

EXAMPLE 2

Inhibition of Cotton Pellet Granuloma in Rats

This model permits the evaluation of a compound's potential to inhibit artificially induced granuloma. The implantation of carrageenin impregnated cotton pellets results in production of large, well-defined granuloma which are easily dissected. The potency of the compounds are assessed by measuring the reduction in granuloma tissue formation.

Preparation of Saline and Carrageenin Cotton Pellets

Cotton wool pellets weighing 40 mg were used for sterilization. Half the number of pellets were dipped in saline and the remaining in 1% aqueous solution (Viscarin® type 402, Marine Colloids Inc. Springfield) until they were soaked well, then squeezed slightly to remove excess saline or carrageenin.

Pellets were dried overnight under a lamp. The pellets in the weight range of 42–44 mg were selected.

Animal Preparation

Rats (in groups of 6, male or female, Charles River, Wistar, weighing 140–150 g) were anaesthetized with ether. The back was shaved and cleaned; swabbed with alcohol and one centimeter incision was made in the lower midback. A small channel was made bilaterally using a blunt forceps and one cotton pellet placed in each channel. Air from the incision was removed and the wound was stitched. The test compound was prepared in 0.5% carboxyl methyl cellulose and was administered orally at a dose of 10, 20 and 30 mg/kg daily for seven days. Three hours after the administration of the last dose on day 7, animals were sacrificed. The pellets were removed by cutting the skin along the dorsal midline and peeling the skin away from the bodywall in both lateral directions. The pellets were weighed and then placed in drying oven at 140° C. overnight. The dry weights were then recorded and the amount of granuloma was assessed by subtracting the original pellet weight from wet weights and dry weights. The data was evaluated using the difference of left and right weights (cf. Table 4).

TABLE 4

Effect of Compound No. 4 on Cotton Pellet Granuloma in Rats.

| Treatment | Dose mg/kg, p.o. × 5 | % Inhibition of granuloma | |
| --- | --- | --- | --- |
| | | Wet wt. | Dry wt. |
| Compound No. 4 | 10 | 21 | 35.6 |
| | 20 | 54 | 89.0 |
| | 30 | 64 | 82.8 |
| Hydrocortisone | 30 | 20.5 | 37.5 |

Compound 4 as representative of the compounds of the present invention inhibits the granuloma formation induced by carrageenin.

EXAMPLE 3

Inhibition of Micro-Anaphylactic Shock of Guinea Pigs

Guinea pigs of either sex weighing between 300–350 g were sensitized with egg albumin absorbed over Al(OH)$_3$ gel. After 21 days of sensitization, each animal was placed in an air tight perspex chamber and exposed to 0.5% egg albumin aerosol through EEL atomizer. EEL atomizer was operated by connecting it to pressurized air through a water trap and dial type sphygmomanometer at the constant air pressure of 180 mm Hg. The time of onset of asthma in seconds and recovery period in minutes was noted.

Each animal was exposed to egg albumin aerosol at an interval of 15 days to maintain the consistency of the reactivity of animals to the antigen. After 3 such control exposures, animals were subjected to drug treatment. On the day of the experiment one group of Guinea pigs consisting of 10 animals was kept as control exposing them only to 0.5% egg albumin aerosol. Another group of 10 guinea pigs was treated with Indomethacin 10 mg/kg i.p. 30 mins. before exposure to the antigen. Yet another group of 10 guinea pigs was pretreated with Indomethacin 10 mg/kg i.p. and 30 mins. after Indomethacin pretreatment the test compound (20 mg/ip) was injected. Fifteen mins. after the administration of the test compound the animals were exposed to 0.5% egg albumin aerosol. Onset time of recovery period of each group was noted (cf. Table 5).

TABLE 5

Effect of Compound No. 4 on microanaphylactic shock of guinea pigs.

| Treatment | Onset Time in secs. | Recovery period in mins. |
|---|---|---|
| Control group | 75 + 8.7 | 37 + 3.4 |
| Indomethacin treated group 10 mg/kg, i.p. | 82.4 + 11.5 | 147.8 + 3.5 |
| Compound 4, 20 mg/kg$^{-1}$, i.p. present invention + pretreatment with indomethacin, 10 mg/kg, i.p. | 149.2 + 25.1 | 77.6 + 4.7 |

Compound 4 as a representative example of the novel compounds of the present invention protects the animals from bronchoconstriction induced by leukotrienes, subsequent to the exposure of egg albumin aerosol.

EXAMPLE 4

Inhibition of IL-1 Release Human Mononuclear Cells

Purification of Mononuclear Cells From Human Blood 10 ml of human blood were carefully drawn from the antecubital vein using a syringe containing 1 ml of a solution of 3.8% sodium citrate. After dilution with 10 ml PM 16 (Serva, Heidelberg, FRG) and underlayering with 15 ml Lymphoprep® (Molter GmbH), the sample was centrifuged at 400×g for 40 min at 20° C. The mononuclear cells forming a white ring between lymphoprep and plasma were carefully aspirated by a syringe, diluted 1:1 with PM 16 and centrifuged again at 400×g for 10 min. The supernatant was washed with 10 ml RPMI 1640 (Gibco, Berlin, FRG), containing additionally 300 mg/l L-glutamine, 25 mmol/l RPM 1640, containing additionally 300 mg/l L-glutamine, 25 mmol/l HEPES, 100 μg/ml streptomycin and 100 μg/ml penicillin. Finally, using a Coulter counter IT, the cell suspension was adjusted to 5×10$^6$ cells/ml. The cells consist of approx. 90% lymphocytes and 10% monocytes.

Stimulation of Interleukin 1 From Human Mononuclear Cells in Vitro

10 μl DMSO/water (1:10, v/v), containing the test compound, was added to 480 μl of a suspension, containing 5×10$^6$ mononuclear cells. The synthesis of IL-1 was stimulated by the addition of 10 μl DSMO/water (1:10, v/v), containing 0,5 μg LPS (Salmonella abortus equi, Sigma). After incubation at 37° C. for 18 hours, the samples were cooled to 0° C. and centrifuged for 1 min. in a table centrifuge. 25 μl aliquots of the supernatant were assayed for IL-1 alpha activity using a commercially available 125-J-IL-1-alpha radioimmunoassay Kit (Amersham/UK), and for IL-1 beta in a similar way using the specific test kit. Control experiments were performed as described without test compound, or with cycloheximide as a test compound.

The effect of compound 4 as inhibitor of LPS stimulated IL-1 alpha (Approx. IC$_{50}$=200–300 nmol/l), is shown in FIG. 1.

Compound 4 as a representative example of the compounds of the present invention inhibits LPS stimulated IL-1 alpha release from human mononuclear cells in vitro.

Compounds of the instant application are prepared as described below:

EXAMPLE 5

Preparation of 1-(2,4,6-Trimethoxyphenyl) cyclohexene

An Example of Formula V Wherein R$_3$=4,6-dimethoxy, R$_2$=CH$_3$ 2,4,6-Trimethoxybromobenzene (1 eqvt.) was placed in a flame dried 3-necked flask under nitrogen. Dry tetrahydrofuran (THF) (983 ml) was added and the reaction mixture was cooled to −30° C. n-BuLi (1.3 eqvt.) in hexane (commercial) was added dropwise and after the addition the reaction mixture was stirred for 30 min. Thin layer chromatographic examination at this stage indicated completion of metallation reaction. Cyclohexanone (1.1 eqvt.) diluted with equal volume of dry THF was added to the reaction mixture at −30° C. and the reaction mixture was stirred for another one hour at −30° C. and later allowed to come to room temperature. Water (150 ml) was added and extracted with ethyl acetate. The ethyl acetate layer was dried over anhydrous sodium sulfate and concentrated. The residue was added to dichloromethane and stirred for 30 min. with a catalytic amount of p-toluenesulphonic acid (9 g). The dichloromethane layer was washed with sodium bicarbonate solution followed by water and dried. The residue was crystallized from diisopropylether to give the title compound; m.p. 127° C., Yield: 64.7%.

EXAMPLE 6

Preparation of trans-(±)-2-(2,4,6-Trimethoxyphenyl) cyclohexanol

An Example of Formula VI Wherein R$_2$=CH$_3$, R$_3$=4,6-dimethoxy and R$_4$=OH

A compound of formula V (from Example 5) (1 eqvt.) was mixed with sodium borohydride (4 eqvt.) and dry THF (2,200 ml). The reaction mixture was cooled to 0° C. under nitrogen and borontrifluoride etherate (5.1 eqvt.) was added dropwise. After the addition was complete, the temperature was raised to 50° C. and stirred for 30 min. The reaction mixture was cooled to room temperature and water was added dropwise to destroy excess diborane. The organoborane was oxidized by simultaneous addition of 30% $H_2O_2$ (248 ml) and 3M NaOH (248 ml) solution. After the addition, the reaction mixture was heated at 50° C. for 3 hours. After completion of oxidation, the reaction mixture was diluted with water and extracted with ethyl acetate. The ethyl acetate layer was dried and concentrated. The crude product was purified by flash chromatography on silica gel using 10% ethyl acetate in pet. ether; m.p. 123° C., Yield: 52%.

EXAMPLE 7

Preparation of trans-(±)-1-[3-(2-Acetoxy) cyclohexyl-2,4,6-trimethoxy]phenyl-1-ethanone Formula VII Wherein $R_3$=4,6-dimethoxy, $R_2$=$CH_3$ and $R_4$=O—CO—$CH_3$ The product from Example 6 (1 eqvt.) was mixed with dry methylene chloride (1520 ml). Acetic anhydride (25 eqvt.) and phosphoric acid (152 ml) were added and stirred at room temperature for one hour. The reaction mixture was worked up by adding sodium carbonate solution until the reaction mixture was alkaline and extracted with dichloromethane. The organic layer was thoroughly washed with water and dried. The crude product after removal of the solvent was crystallized from pet. ether; m.p. 87° C., Yield: 84%.

EXAMPLE 8

Preparation of trans-(±)-1-[3-(2-Acetoxy) cyclohexyl-4,6-dimethoxy-2-hydroxy]phenyl-1-ethanone Formula VII Wherein $R_2$=H, $R_3$=4,6-dimethoxy and $R_4$=O—CO—$CH_3$ The product from Example 7 (1 eqvt.) was mixed with dry dichloromethane (5,450 ml) and cooled to 0° C. Borontribromide (1.1 eqvt.) was added with a syringe and stirred at 0° C. for one hour. Water was added carefully and the product was extracted with ethyl acetate, washed with water, and dried over anhydrous sodium sulfate. The crude product was crystallized from ethyl acetate; m.p. 151° C., yield: 70–71%.

EXAMPLE 9

Preparation of trans--(±)-2-[3-Acetyl-4,6-dimethoxy-2-hydroxy]phenylcyclohexanol Formula VII Wherein $R_2$=H, $R_3$=4,6-dimethoxy, and $R_4$=OH The product from Example 8 (1 eqvt.) was stirred under nitrogen atmosphere with methanolic potassium hydroxide solution (20 eqvt., MeOH:water:3:1) for six hours. The reaction mixture was acidified with dil. HCl and the precipitate was filtered off, washed, dried and crystallized from ethylacetate; m.p. 161° C., Yield: 88–89%.

EXAMPLE 10

Preparation of trans-(±)-2-[4,6-Dimethoxy-2-hydroxy-3-(3-(4-chlorophenyl)prop-2-(E)-enoyl)] phenylcyclohexanol Formula II Wherein $R_1$=4-chlorophenyl, a=Another Bond, $R_2$=H, $R_3$=4,6-dimethoxy and $R_4$=OH The product from Example 9 (1 eqvt.) was stirred with 4-chlorobenzaldehyde (3 eqvt.) and 10% alcoholic sodium hydroxide (30 eqvt.) at room temperature for 24 hours. The reaction mixture was acidified with the dil. HCl at 0° C. to pH 5 and the orange precipitate was collected by filtration. Recrystallized from ethyl alcohol; m.p. 221° C., yield: 60%.

EXAMPLE 11

Preparation of trans-(±)-2-(4,6-Dimethoxy-2-hydroxy-3-(3-(4-chlorophenyl)propanoyl)] phenylcyclohexanol Formula II Wherein $R_1$=4-chlorophenyl, a=No Bond, $R_2$=H, $R_3$=4,6-dimethoxy and $R_4$=OH The product from Example 10 was stirred with 10% pd/c (5 mol %) in ethyl alcohol and under hydrogen overnight. The catalyst was filtered off and the solvent concentrated to give the product; m.p. 190° C., Yield: 90%.

EXAMPLE 12

An Alternative Preparation of trans-(±)-2-[2,4,6-trimethoxy)phenylcyclohexanol

Formula VI Wherein $R_2$=$CH_3$, $R_3$=4,6-dimethoxy and $R_4$=OH 2,4,6-Trimethoxybenzene (1 eqvt.), cyclohexene oxide (1.5 eqvt.) and dry dichloromethane (840 ml) were placed in a 3-necked r.b flask equipped with a stirrer. The reaction mixture was cooled to –78° C. and aluminum chloride (1.5 eqvt.) was added in small portions over a period of one hour. The stirring was continued for an additional period of three hours. The reaction mixture was worked up by addition of water and extracted with ethyl acetate. The crude product was crystallized from petroleum ether; m.p. 123° C., Yield: 63–64%.

EXAMPLE 13

Resolution of (±)-trans-2-(2,4,6-trimethoxy) phenylcyclohexanol

A Compound of Formula VI Wherein $R_2$=H, $R_3$=4,6-dimethoxy and $R_4$=OH (±) trans-2-(2,4,6-Trimethoxy)phenylcyclohexanol (50.0 g; 0.18797 mol), 3-nitrophthalic anhydride (26.399 g; 0.18797 mol) and pyridine (42.18 ml; 2.78×0.18797 mol) were heated at 100° under $N_2$ atmosphere for three hours. The reaction mixture was cooled to 0° C., neutralized with 2N HCl and the product obtained extracted with chloroform. The residue after evaporation of solvent was crystallized from methanol (400 ml) to give the crystals of compound of the formula VI, wherein $R_4$ is 3-nitrophthalyloxy (59.0 g; m.p. 198–200°). The hemi acid (0.1285 mol) was treated with (+) cinchonine (37.85 g; 0.1285 mol) in methanol (250 ml) on a steam bath for 30 minutes. Solvent was removed at reduced pressure and the residual salt [96.5 g, OR (+) 84.75° (Hg, 578)] crystallized from ethyl acetate pet. ether (1:1 1400 ml) to afford the crystals (45.0 g; OR (+) 75.11° (Hg 578) and a mother liquor [50.0 g; OR (+) 97.30° (Hg, 579)].

The crystals (45.0 g) on further crystallizations (thrice) from ethyl acetate-pet. ether afforded enriched cinchonine salt [31.0 g, OR (+) 71.08° (Hg, 578)]. The enriched salt on treatment with 2N HCl at 0° gave the resolved (–) compound of the formula VI, wherein $R_4$ is 3-nitrophthalyloxy [16.1 g; OR (–) 37.15° (Hg, 578). The hemi acid on hydrolysis with 7.5% KOH solution in methanol-water (1:2, 5878 ml) at reflux temperature, followed by crystallization of the product from ethyl acetate-pet. ether (24:160 ml) yielded (–)- trans-2-(2,4,6-trimethoxy)phenylcyclo-hexanol [7.0 g; OR (−) 43.430 (Hg, 578)].

The mother liquor (50.0 g) was treated with 2N HCl at 0° and the product was subjected to crystallizations (thrice) from ethyl acetate-pet. ether to give the crystals of the resolved (+) compound of formula VI; wherein $R_4$ is 3-nitrophthalyloxy [15.1 g; OR (+) 35.65° (Hg, 578)]. The hemi acid on hydrolysis with 7.5% KOH solution in methanol-water (1:2; 548.5 ml) at reflux temperature for 60 hours followed by crystallization of the product from ethyl acetate-pet. ether (25:150 ml) yielded (+) trans-2-(2,4,6-trimethoxy)phenylcyclohexanol [7.24 g; OR (+) 42.30° (Hg, 578)].

EXAMPLE 14

Preparation of trans-(+/−)-2-[4,6-dimethoxy-2-hydroxy-3-(3-(3-bromophenyl)prop-2-(E)-enoyl] phenylcyclohexanol The product from Example 9 (1 eqvt.) was stirred with 3-bromobenzaldehyde (3 eqvt.) and 10% sodium hydroxide solution (10 eqvt. in 1:1 ethanol-water) at room temperature for 4 hours. The reaction mixture was diluted with ice-cold water and filtered. The orange residue on chromatographic purification over silica-gel furnished the title compound; m.p. 172–74° C., yield: 64%.

EXAMPLE 15

Preparation of trans-(+/−)-[4,6-dimethoxy-2-hydroxy-3-(3-(3-bromophenyl)prop-2-(E)-enoyl) phenyl]cyclohexyl-2-(S)-carb-tertbutoxyamino propanoate The product from Example 14 (1 eqvt.) was stirred with 2-(S)-carb-tert-butoxyamino propanoic acid (1.5 eqvt.) and 4-dimethylaminopyridine (0.2 eqvt.) in dichloromethane (2,174 ml). Dicyclohexylcarbodiimide (1.5 eqvt.) in dichloromethane (1,176 ml) was added slowly using an addition funnel at room temperature and stirred for 1 hour. Dichloromethane was removed at a rotary evaporator and the residue crystallized from ethanol (1,450 ml) to afford the title compound was stirred with ether. The precipitated dicyclohexyl urea was filtered out. The filtrate was concentrated and the residue was chromatographed over silica-gel. The fractions enriched with less polar (tlc) diasteriomer were concentrated and the residue stirred with ethyl acetate-pet. ether (5,882 ml; 1:10) to afford the title compound; m.p. 139–44° C., yield: 30%. [HPLC: column-$\mu$-porosil, detection—247 nm, flow rate—1.5 ml/min., mobile phase—hexane:ethyl acetate (80:20), assay—94.6%, retention time—13.7 min.].

EXAMPLE 16

Preparation of trans-(−)-2-[4,6-dimethoxy-2-hydroxy-3-(3-(3-bromophenyl)prop-2-(E)-enoyl) phenyl]cyclohexyl-2-(S)-amino propanoate hydrochloride The product from Example 15 (1 eqvt.) was stirred with anisole (6 eqvt.) at 0° C. Cold formic acid (200 eqvt.) was added slowly through an addition funnel and stirred at that temperature for 10 minutes. The temperature was then raised slowly (over 1.5 hours) to 20° C. and stirred at that temperature for 2 hours. Formic acid was removed completely in-vacuo (bath temperature 22° C.). The residue was stirred with dichloromethane (5,550 ml) at 0° C. and charged with etherial HCl (5,550 ml). The reaction mixture was stirred for 25–30 minutes and the solvents were removed at vacuum (bath temperature 22° C.). The oily residue was dissolved in dichloromethane (925 ml) and slowly charged with hexane (4,625 ml) while stirring. The supernant was decanted off and the gummy residue was again dissolved in dichloromethane (925 ml) and charged with hexane (4,625 ml) while stirring. The supernant was decanted off and the powdery residue was dried at high vacuum; m.p. 138–40° C., yield: 88% [HPLC: column—C18 nucleosil, detection—220 nm, flow rate—1.5 ml/min., mobile phase—water:acetonitrile:triethyl amine (40:60:0.1%) pH adjusted to 3.0 with orthophosphoric acid, assay—99.95%, retention time—5.43 min.]

The following is a sequence for the synthesis of Compound No. 9 of Table 2 and a description of the synthesis procedure therefor.

Sequence for the Synthesis of Compound No. 9 of Table 2

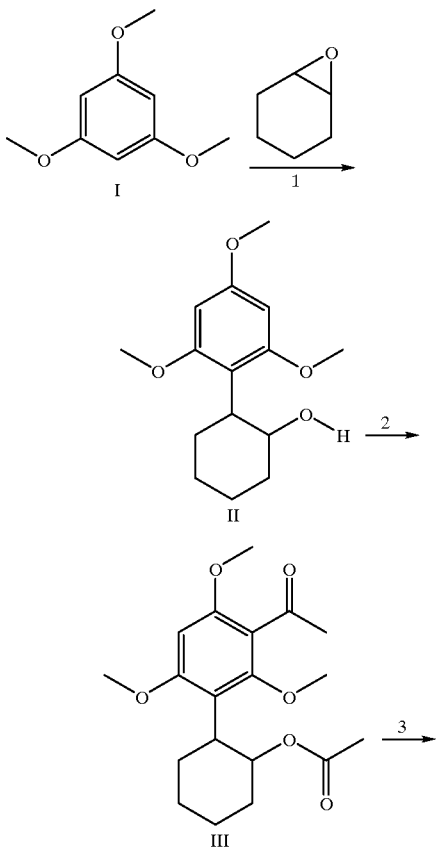

-continued
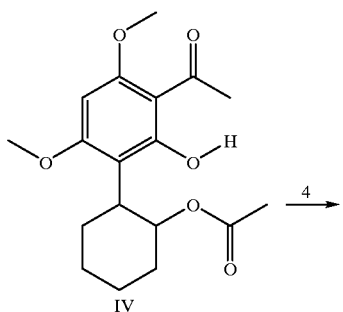
IV
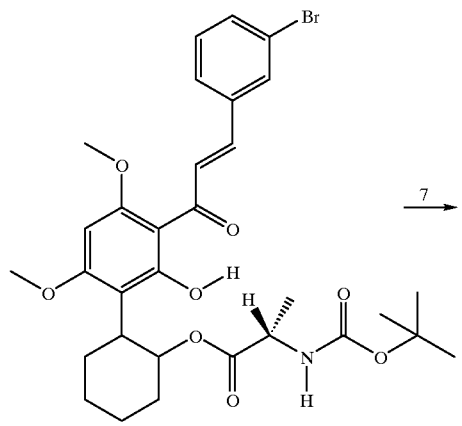
(Mixture of diasteriomers)
VII
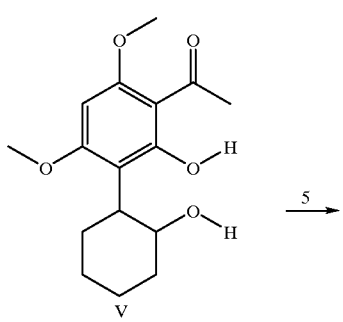
V
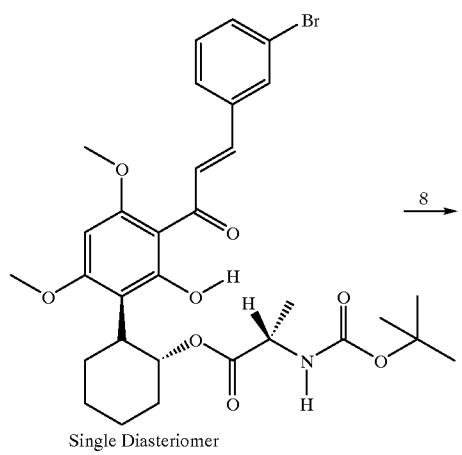
Single Diasteriomer
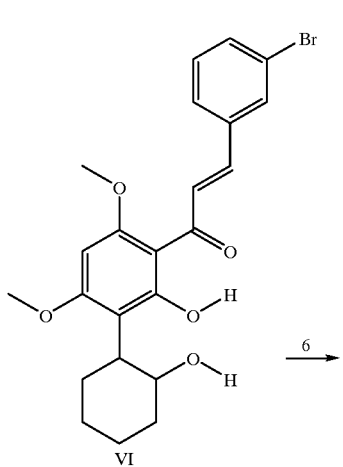
VI
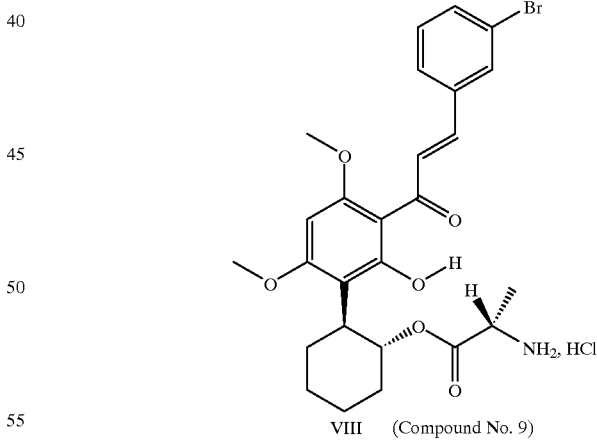
VIII  (Compound No. 9)
1. AlCl$_3$, CH$_2$Cl$_2$
2. Ac$_2$O, H$_3$PO$_4$, CH$_2$Cl$_2$
3. BBr$_3$, CH$_2$Cl$_2$
4. 5% NaOH in 3:1 MeOH, H$_2$O
5. 3-Bromobenzaldehyde, 10% NaOH in 1:1 EtOH, H$_2$O
6. BOC-Alanine, DCC, DMAP, CH$_2$Cl$_2$
7. Chromatography
8. a) HCOOH, Anisole; b) Etherial HCl, CH$_2$Cl$_2$ Synthesis Procedure for Compound No. 9 of Table 2

1. trans-(+/−)-2-(2,4,6-Trimethoxyphenyl)cyclohexanol (II)

Cyclohexene oxide (90.2 ml; 0.89 mol) was added dropwise to a mechanically stirred mixture of trimethoxybenzene (I, 100 g; 0.594 mol) and aluminum chloride (118.82 g; 0.89 mol) in dichloromethane (500 ml) cooled at −78° C. The addition was done over a period of 50 min. The reaction mixture was allowed to stir at that temperature and the progress of the reaction monitored by TLC (tlc system 25% ethyl acetate-pet ether; anisaldehyde spray; pdt. Rf-value 0.35). The reaction mixture was worked up after 3 hours by adding cold-water (400 ml) and extracting with ethyl acetate (4×400 ml). The combined organic layers were washed with water, brine, and dried over sodium sulphate. The solvents were removed in-vacuo at a rotary evaporator. The oily residue was crystallized from pet ether (400 ml) to get the crystals of the title compound (62 g). The mother liquor, on evaporation of the solvents followed by chromatography over silica gel (column diam. 9.5 cm; silica gel 800 g; eluent 10, 25 and 40% ethyl acetate-pet ether), gave 28 g of the title compound. In total, 90 g (yield 57%; mp. 125–27° C.) of the title compound was isolated.

2. trans-(+/−)-2-(3-Acetyl-2,4,6-trimethoxyphenyl)cyclohexyl acetate (III)

Acetic anhydride (660 ml; 6.975 mol) was added to the solution of the trans-(+/−)-2-(2,4,6-trimethoxyphenyl)cyclohexanol (II; 60 g; 0.225 mol) in dichloromethane (300 ml) at room temperature, while stirring. It was followed by the dropwise addition of orthophosphoric acid (85%; 40 ml; 0.347 mol) over 45 min. Reaction progress was monitored by TLC (tlc system 30% ethyl acetate-pet ether; spray reagent—anisaldehyde; product Rf—value=0.5). TLC of the reaction mixture after 15 min. revealed complete consumption of the starting material. The reaction mixture was then diluted with 250 ml of cold water, neutralized with solid sodium bicarbonate and extracted with dichloromethane (3×500 ml). The combined organic layer was washed with bicarbonate solution, water, brine and dried over sodium sulphate. It was then concentrated in-vacuo and the residue chromatographed over silica gel (column diam. 9.0 cm; silica gel—1 kg; eluent—5% and 10% ethyl acetate-pet ether) to get the title compound (64 gm; yield 81%; m.p. 82–85° C.).

3. trans-2-(3-Acetyl-4,6-dimethoxy-2-hydroxyphenyl)cyclohoxyl acetate (IV)

Boron tribromide (16.3 ml; 0.176 mol) dissolved in 250 ml of dichloromethane was added slowly to the solution of the trans-2-(3-acetyl-2,4,6-trimethoxyphenyl)cyclohexyl acetate (III; 56 g; 0.160 mol) in dichloromethane (350 ml) at 0° C. over 30 min. The reaction progress was monitored by TLC (tlc system 5% ethyl acetate-pet ether; anisaldehyde spray; pdt. Rf value—0.6); TLC of the reaction mixture after 15 min. indicated complete consumption of the starting material. The reaction mixture was then diluted with 250 ml of water and poured into saturated bicarbonate solution and extracted with dichloromethane (3×500 ml). The combined organic layer was washed with bicarbonate, water, brine, and dried over sodium sulphate. Solvents were removed at the rotary evaporator and the residue triturated with ethyl acetate-pet ether (100 ml; 1:1). The solid was filtered at suction and dried at high vacuum to get 34 g of the title compound. The mother liquor was chromatographed over silica gel (column diam. 5 cm; silica gel 150 g; eluent 10% ethyl acetate-pet ether) to get 9 g of the title compound. The total amount of the title compound isolated was 43 g (yield 80%; mp. 155–57° C.).

4. trans-2-(3-Acetyl-4,6-dimethoxy-2-hydroxyphenyl)cyclohexanol (V)

To a suspension of trans-2-(3-acetyl-4,6,-dimethoxy-2-hydroxyphenyl)cyclohexyl acetate (IV; 43 g; 0.128 mol) in methanol (460 ml) was added a solution of sodium hydroxide (20%; 154 ml) using the addition funnel and allowed to stir at room temperature for 15 min. The reaction mixture was then heated to 60° C. and the progress of the reaction monitored by TLC (tlc system 10% ethyl acetate-chloroform; anisaldehyde spray; pdt. Rf value 0.3). Complete consumption of the starting material was seen after stirring at 60° C. for 3 hours. The reaction mixture was then cooled in an ice bath and neutralized with 2N HCl. The precipitated solid was filtered and dried at high vacuum (dry solid 32 g). The filtrate was concentrated in-vacuo to remove methanol and extracted with ethyl acetate. The ethyl acetate layer was washed with water, brine and dried over sodium sulphate. It was concentrated and chromatographed over silica gel (eluent 3% ethyl acetate-chloroform) to get 3 g of the title compound. In total, 35 g of the title compound was isolated (yield 93%; mp. 162–64° C.).

5. trans(+/−)-2-[4,6-Dimethoxy-2-hydroxy-3-(3-(3-bromophenyl)prop-2-(E)-enoyl)]phenyl cyclohexanol (VI)

A cold solution of sodium hydroxide (20%; 500 ml) was added slowly using the addition funnel to a solution of trans-2-(3-acetyl-4,6-dimethoxy-2-hydroxyphenyl)cyclohexanol (V; 72 g; 0.244 mol) and 3-bromobenzaldehyde (85.34 ml; 0.732 mol) in 500 ml of ethanol at room temperature and progress of the reaction monitored by TLC (tlc system 10% ethyl acetate-chloroform; UV detection). TLC of the reaction mixture after 4 hours revealed complete consumption of the starting material. The reaction mixture was diluted with ice-cold water (1000 ml) and the precipitated solid was filtered out. The residue after chromatography over silica gel (column diam. 9.5 cm; silica gel 1.5 Kg; eluent chloroform and 2% ethyl acetate-chloroform) furnished 21 g of the title compound. The filtrate on extraction with ethyl acetate followed by concentration and chromatography of the residue over silica gel (column diam. 5.5 cm; silica gel 400 g; eluent 50% chloroform-pet ether; chloroform and 2% ethyl acetate-chloroform) gave 4 g of the title compound. In total, 25 g of the title compound was isolated (yield 63.72%; mp. 172–74° C.).

6. trans(+/−)-2-[4,6-Dimethoxy-2-hydroxy-3-(3-(3-bromophenyl)prop-2-(E)-enoyl)-phenyl]cyclohexyl-2-(S)-carb-tertbutoxyamino propanoate (VII)

To the stirred mixture of trans(+/−)-2-[4,6-dimethoxy-2-hydroxy-3-(3-bromophenyl)prop-2-enoyl)]phenyl cyclohexanol (VI; 85 g; 0.184 mol), 2-(S)-carb-tert-butoxyamino propanoic acid (52.22 g; 0.276 mol), and dimethylaminopyridine (4.25 g; 5% by weight of VII) in dichloromethane (400 ml) was slowly added a solution of dicyclohexyl carbodiimide (57 g; 0.276 mol) in dichloromethane (220 ml) using an addition funnel at room temperature. Reaction progress was monitored by TLC (tlc system 40% ethyl acetate-pet ether or 20% ethyl acetate, 20% chloroform-pet ether; UV detection; pdt. Rf value 0.8). TLC of the reaction mixture after 1 hour revealed complete consumption of the starting material. Dichloromethane was removed at the rotary evaporator and the residue stirred with ether. The precipitated dicyclohexylurea was filtered out. The filtrate was concentrated at the rotary evaporator and the residue chromatographed over silica gel (column diameter 10.5 cm; silica gel 1 Kg; eluent 5% and 10% ethyl acetate-pet ether). The fractions enriched with less polar diasteriomer (tlc) were mixed together and concentrated. The residue was stirred with ethyl acetate-pet ether (1300 ml/1:12) and the precipitated solid was filtered out. This solid was again stirred with ethyl acetate-pet ether (1100 ml; 1:10) and filtered to give 34.5 g of the pure title compound (HPLC) as a yellow orange solid (yield 30%).

7. trans(−)-2-[4,6-Dimethoxy-2-hydroxy-3-(3-(3-bromophenyl)prop-2-enoyl)-phenyl]cyclohexyl-2-(S)-aminopropanoate hydrochloride (VIII)

A cold formic acid (408 ml; 10.8 mol) was added slowly through the addition funnel to the precooled (0° C.) suspension of trans(−)-2-[4,6-dimethoxy-2-hydroxy-3-(3-(3-bromophenyl)prop-2-enoyl)phenyl]cyclohexyl-2-(S)-carb-tert-butoxyamino propanoate (34 g; 0.054 ml) in anisole (34 ml; 0.313 mol), over a period of 15 min. The reaction mixture was stirred at that temperature for 10 min. Then the temperature was allowed to rise slowly (over 1.5 hours) to 20° C. and stirred at that temperature for 2 hours. TLC (tlc system 10% methanol-chloroform; UV detection; pdt. Rf value 0.6) of the reaction mixture showed complete consumption of the starting material. Formic acid was removed completely in-vacuo (bath temperature 22° C.). The residue was stirred with toluene and the toluene stripped off in-vacuo (bath temperature 22° C.) to remove the traces of formic acid. The residue, i.e., trans-2-[4,6-dimethoxy-2-hydroxy-3-(3-(3-bromophenyl)prop-2-enoyl)phenyl] cyclohexyl-2-(S)-aminopropanoate formate salt, was immediately subjected to the hydrochloride formation as follows.

Etherial HCl (300 ml) was added slowly using an addition funnel to the precooled (0° C.) solution of the formate salt in dichloromethane (300 ml) and stirred at that temp. for 25–30 min. Solvents were removed in-vacuo (bath temperature 20–22° C.). The oily residue was then dissolved in dichloromethane (50 ml) and slowly charged with hexane (250 ml), whilst stirring. The stirring was then stopped and the reaction mixture allowed to settle. The supernatant was decanted off. The gummy residue was again stirred with 50 ml of dichloromethane and 300 ml of hexane. The supernatant was decanted off and the residue stirred thrice with hexane (300 ml each time). The supernatants were decanted off and the powdery residue was dried at high vacuum (bath temperature 50° C.) to get the title compound (27 g; yield 88%).

| HPLC details of Compound No. 9 of Table 2: | |
|---|---|
| Retention time: | 5.43 min. |
| Detection: | 220 nm |
| Assay (purity): | 99.95% |
| Flow rate: | 1.5 ml/min. |
| Mobile phase: | Water-acetonitrile-triethylamine; |

| -continued | |
|---|---|
| HPLC details of Compound No. 9 of Table 2: | |
| | (40:60:0.1%) |
| | (pH adjusted to 3.0 with |
| | orthophosphoric acid) |
| Column: | C18, Nucleosil |

Pharmacological Profile of Compound No. 9 of Table 2

EXAMPLE 17

Effect on Adjuvant-Induced Arthritis in Rats

Adjuvant-induced arthritis in the rat is a model which permits the evaluation of the potential of a compound to inhibit an arthritic condition in rats which is similar to the human rheumatoid arthritis. This model differentiates between the immunomodulatory and anti-inflammatory potential of the compound. The potency of the test compound is statistically assessed by measuring the reduction in the volumes of both injected and uninjected hind paws in comparison with the control (untreated) group.

Method

Figure 2:
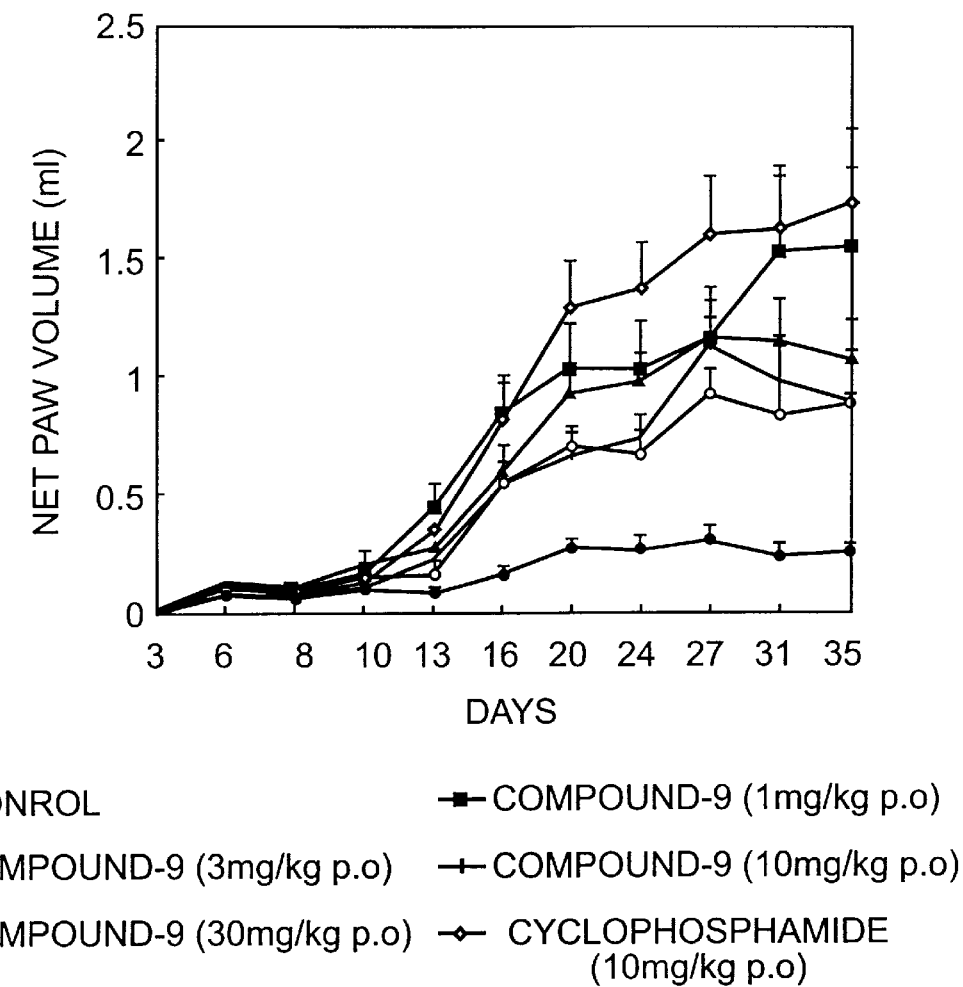
FIG. 2 is a graph illustrating the effect of Compound 9 of Table 2 at varying dosages on adjuvant arthritis in rats (uninjected paw)
Figure 3:
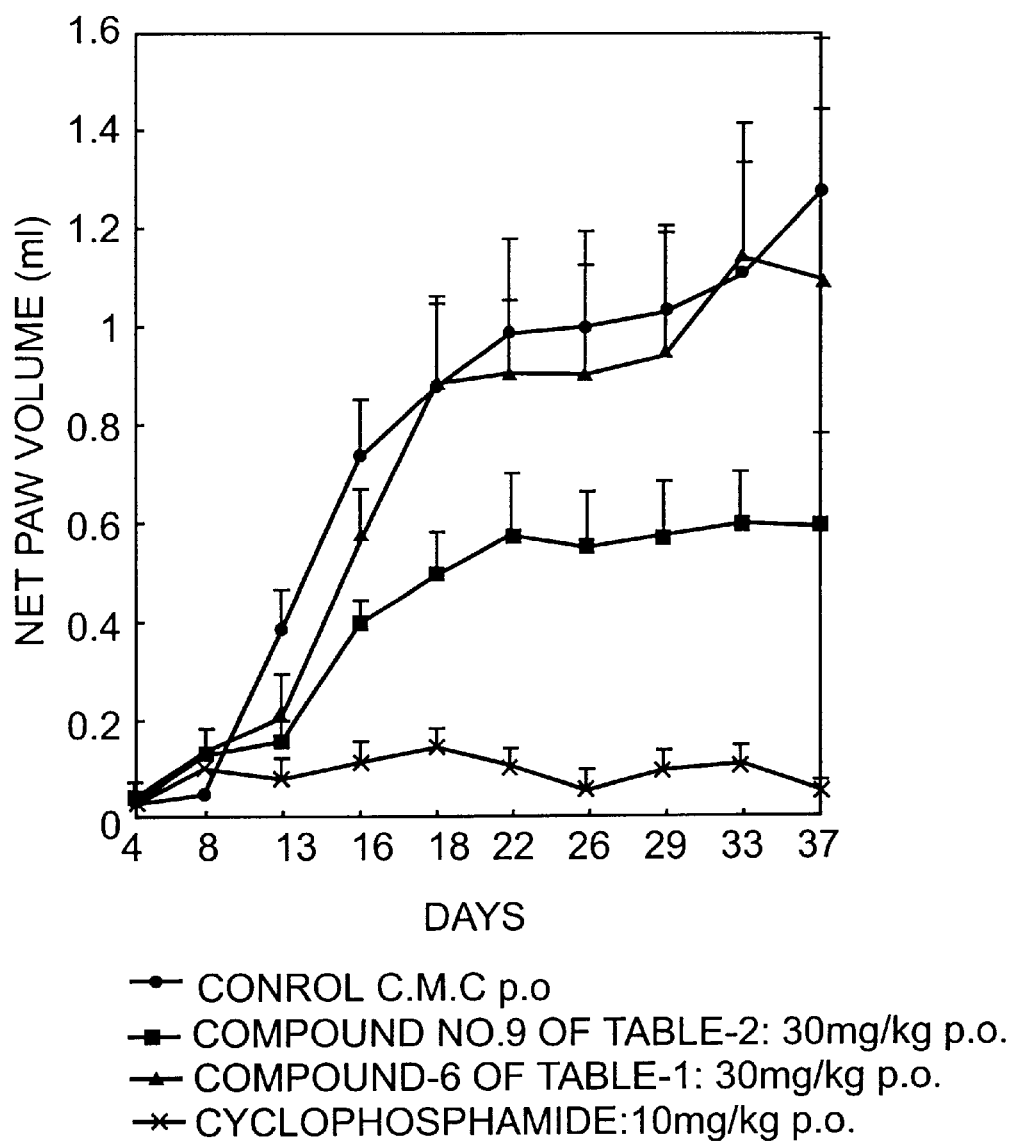
FIG. 3 is a graph comparing the effect of Compound 6 of Table 1 and Compound 9 of Table 2 on adjuvant arthritis in rats (uninjected paw)

Female Wistar rats (120–150 g) were randomly distributed in groups of 10 rats each, after receiving 0.1 ml of a 1% suspension of *Mycobacterium tuberculi* in paraffin oil intrapedally into one hind paw (injected paw). Contralateral hind paw (uninjected paw) developed secondary lesions in about 10 days time, which were due to the development of an immune reaction. Drug treatment was started on the day of induction of arthritis and continued for 12 days. Treatments included different doses of the test compound and the standard compound viz, cyclophosphamide. Paw volume measurements were done using a water plethysmometer on day one and thereafter for the period of 35–40 days. The volumes of both injected and uninjected hind paws were monitored in control (untreated) as well as treated groups. Compound 9 of Table 2 was administered at the doses of 1, 3, 10, 30 mg/kg orally once a day. The test compound showed significant and dose dependent reduction in the uninjected paw volumes at doses 3, 10, and 30 mg/kg; as shown in FIG. 2. This activity is to be contrasted with the activity for the representative compound, compound 6 of Table 1, which when fed orally at 30 mg/kg once every day for 12 days showed very slight reduction in the uninjected paw volume (FIG. 3) compared to control, demonstrating thereby the superiority of compound 9 of Table 2 in this activity.

EXAMPLE 18

Effect on Experimental Allergic Encephalomyelitis (EAE) in Guinea Pigs

This method permits the evaluation of the potential of the test compound in preventing the development of an autoimmune disorder leading to demyelination in the guinea pigs which can be equated to multiple sclerosis disease in humans. EAE is a reproducible chronic inflammatory autoimmune disease of the central nervous system in which an animal is immunized with either a homologous or heterologous extract of the whole brain and spinal cord, which contains the basic myelin protein together with Freund's Complete Adjuvant (FCA). A pathological condition would set in during ten to twenty days following immunization, which is characterized by weight loss, abnormal gait, mild to severe ataxia, paraparesis and moribund state leading to death. The potential of the test compounds to prevent this autoimmune condition was evaluated by observing the severity of the disease and mortality in comparison with untreated and hydrocortisone (standard drug) treated animals.

Method

Figure 4:
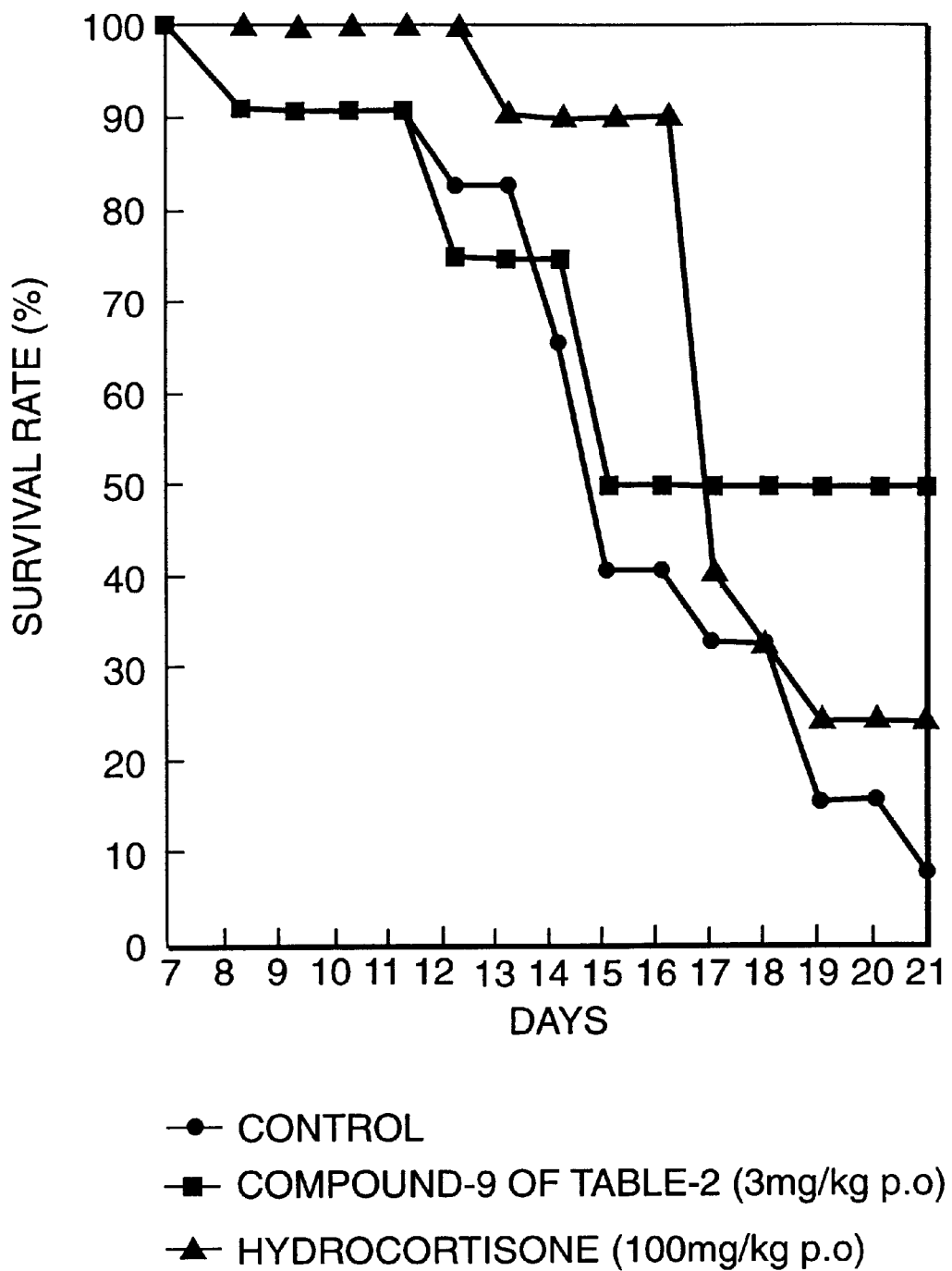
FIG. 4 is a graph illustrating the effect of Compound 9 of Table 2 on EAE (survival rate in %) in guinea pigs.
Figure 5:
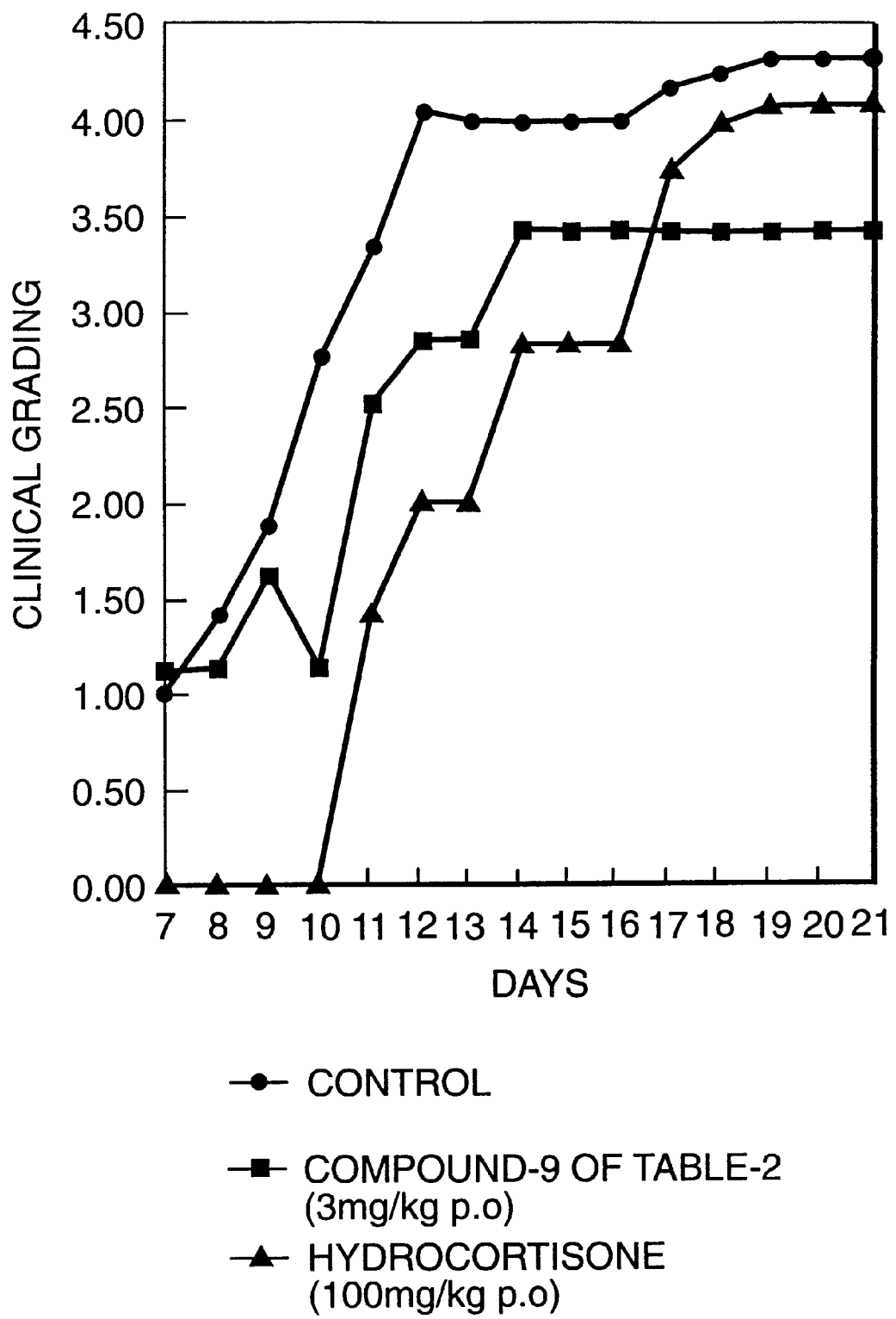
FIG. 5 is a graph illustrating the effect of Compound 9 of Table 2 on EAE (clinical grading) in guinea pigs.

Guinea pigs (200–300 g) were randomly distributed into groups of 10 each after receiving 0.075 ml of it brain and spinal cord extract in FCA intradermally on the back and 0.050 ml intrapedally in one hind paw. Compound 9 of Table 2 was administered orally at 3 mg/kg once daily for 10 days. The standard compound was administered 100 mg/kg p.o. once daily for 10 days. The weights of the animals were noted every day. Eight days after the induction of the disease, the animals were rated regularly for the severity of the disease and mortality was monitored. The test compound reduced the mortality rate by 45% while hydrocortisone produced only 21% reduction in the mortality as shown in FIG. 4. Also the clinical symptoms were significantly reduced in the test compound treated group as compared to the untreated group as shown in FIG. 5.

EXAMPLE 19

Oral bioavailability in the Rat and Dog

Since the test compound produced significant activity in the adjuvant arthritic rats and experimental allergic encephalomyelitic guinea pigs when administered orally, the extent of oral bioavailability of this compound was estimated in rats and dogs. Compound 9 of Table 2 was administered intravenously (1 mg/kg) to conscious rats and dogs and blood samples were collected at various time points after administration. Similarly, the test compound was also administered orally (10 mg/kg) to a different set of rats and dogs and blood samples were collected at various time points. The blood samples were extracted and were analyzed by HPLC to obtain the concentration of compound 9 in the plasma. The plasma levels obtained after intravenous and oral administration were plotted against time, areas under the curves were calculated and percent bioavailability were estimated. The test compound showed 46% oral bioavailability in the rat and 73% oral bioavailability in dog as shown in Table 6. The extent of oral bioavailability in different species clearly indicates that compound 9 of Table 2, a representative example of the compounds of the present invention can be administered orally as a therapeutic agent.

TABLE 6

| Species | Dose mg/kg (Oral) | % Bioavailability |
| --- | --- | --- |
| Rat | 10 | 46 |
| Dog | 10 | 73 |

We claim:

1. A compound of formula I

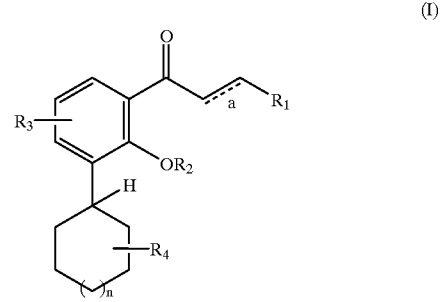

wherein $R_1$ denotes $C_1$–$C_6$-alkyl, substituted $C_1$–$C_6$-alkyl, C(O) O—$C_1$–$C_4$-alkyl, C(O)OH, or a residue selected from

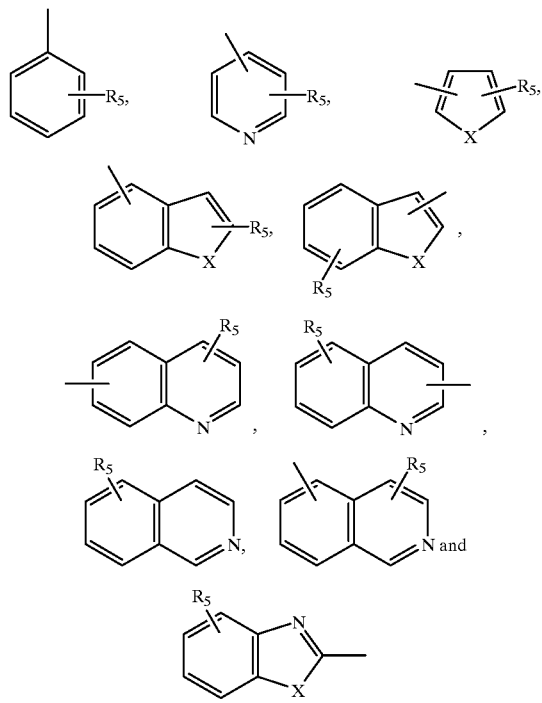

wherein $R_5$ is one, two, three, or four of the residues which are independent of each other and selected from the group consisting of H, $C_1$–$C_6$-alkyl, substituted $C_1$–$C_6$-alkyl, hydroxy, $C_1$–$C_6$-alkoxy, carboxy, cyano, NHC(O)$C_1$–$C_3$-alkyl, —O$C_1$–$C_3$-alkyl-phenyl, $C_1$–$C_4$-alkyl-O—$C_1$–$C_4$-alkyl, —O—C(O)—$C_1$–$C_4$-alkyl, —C(O)—O—$C_1$–$C_4$-alkyl, halogen, amino, nitro, —NH—$C_1$–$C_4$-alkyl, —N—($C_1$–$C_4$-alkyl)$_2$, and —$C_1$–$C_4$-alkyl-$R_6$ wherein $R_6$ is a residue selected from

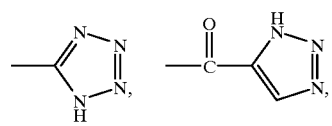

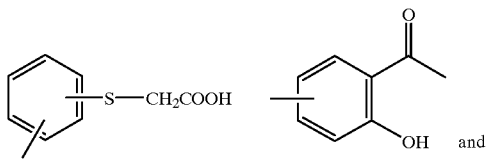 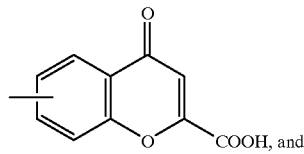 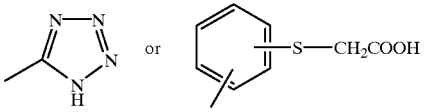

X is O, S, N—H, N—$C_1$-$C_6$-alkyl;

$R_2$ is H, $C_1$-$C_6$-alkyl, —C(O)—$C_1$-$C_6$-alkyl;

$R_3$ is one, two, or three of the residues which are independent of each other and selected from the group consisting of H, $C_1$-$C_6$-alkyl, —C(O)—$C_1$-$C_6$-alkyl, —C(O)—O—$C_1$-$C_6$-alkyl, OH, O—$C_1$-$C_6$-alkyl, —O—C(O)—$C_1$-$C_6$-alkyl, halogen;

$R_4$ is H, —OH, —O—$C_1$-$C_6$-alkyl, —O—C(O)—$C_1$-$C_6$-alkyl, —C(O)—OH, —C(O)—O—$C_1$-$C_6$-alkyl, O—C(O)—($C_1$-$C_4$-alkyl)-$NH_2$, O—C(O)—($C_1$-$C_4$-alkyl-NH—($C_1$-$C_4$-alkyl), O—C(O)—($C_1$-$C_4$-alkyl)-N—($C_1$-$C_4$-alkyl)$_2$, n=0, 1 or 2 and a represents an optional additional single bond, or a physiologically tolerable salt thereof.

2. A compound of formula I as claimed in claim 1, wherein said compound has the formula

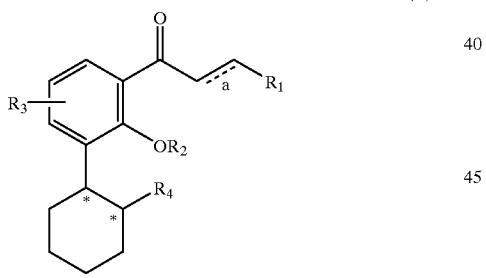

wherein $R_1$, $R_2$, $R_3$, $R_4$ and a are as previously defined, or a physiologically tolerable salt thereof.

3. A compound of formula I as claimed in claim 1, in which $R_1$ is

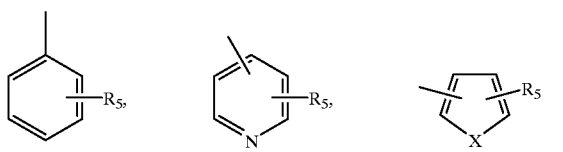

$R_5$ denoting H, $C_1$-$C_6$-alkyl, substituted $C_1$-$C_6$-alkyl, hydroxy, $C_1$-$C_3$-alkoxy, halogen, $C_1$-$C_4$-alkyl-$R_6$ wherein $R_6$ stands for $R_4$ denotes H, OH or —O—C(O)—($C_1$-$C_4$-alkyl)-$NH_2$;

X stands for O, NH, S, N—$C_1$-$C_6$-alkyl; and a stands for an optional additional bond, or a physiologically tolerable salt thereof.

4. A process for the production of a compound of formula I as claimed in claim 1 wherein a compound of formula V

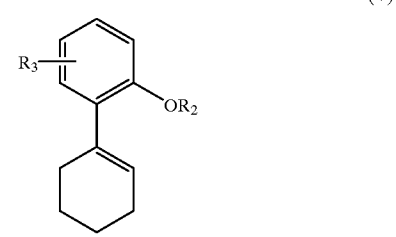

A) is converted into a compound of formula VI, $R_4$ denoting OH

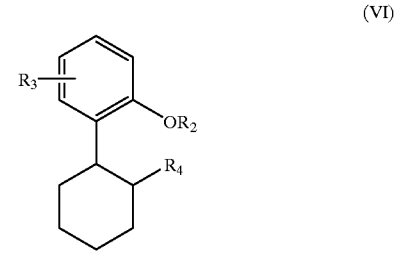

by treatment with a borane-solvent-complex followed by oxidation or

B) to get a compound of formula VI, a compound of formula V is treated with a peracid and the epoxide thus produced is treated with a hydride reagent or C) the compound of formula VI is produced by condensation of a suitable arene with cyclohexene oxide in the presence of an acid catalyst and D) a compound of formula VI is treated with acetic anhydride and a mineral acid to give a compound of formula VII,

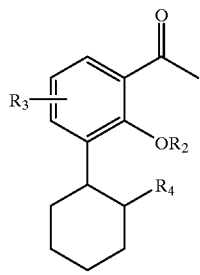

(VII)

wherein R$_2$ is methyl and R$_4$ is O—C(O)—Me and

E) a compound of formula VII as described under D) is demethylated by treatment with a Lewis acid or a demethylating agent to give a compound of formula VII wherein R$_2$ denotes H and R$_4$ denotes OC(O)Me and F) a compound of formula VII wherein R$_2$ denotes H and R$_4$ denotes OH is produced by treatment of a compound produced under E) with dilute alkali, and G) the compound of formula VII is converted into a compound of formula I (a=additional bond) by treatment with an appropriate aldehyde in the presence of a base and a compound of formula I (a=no additional bond) is produced by hydrogenation of the compound of formula I (a=additional bond), R$_1$, R$_2$ and R$_3$, where not explained explicitly, having the meaning as defined in claim 1.

5. A pharmaceutical composition containing an effective amount for the treatment of inflammatory conditions of at least one compound of the formula I or physiologically tolerated salt thereof as claimed in claim 1 together with a pharmaceutically acceptable carrier.

6. A method for the treatment of inflammatory conditions, which comprises administering an effective amount of at least one compound of the formula I or physiologically tolerated salt thereof as claimed in claim 1 to a host in need of such treatment.

7. A method as claimed in claim 6 for the treatment of chronic inflammatory conditions.

* * * * *